(12) United States Patent
Miyazaki et al.

(10) Patent No.: US 9,954,183 B2
(45) Date of Patent: Apr. 24, 2018

(54) INTERMEDIATE FOR HETEROACENE COMPOUND AND SYNTHETIC METHOD OF HETEROACENE COMPOUND USING ITS INTERMEDIATE

(71) Applicant: Samsung Electronics Co., Ltd., Suwon-si, Gyeonggi-do (KR)

(72) Inventors: Eigo Miyazaki, Hwaseong-si (KR); Jeong Il Park, Seongnam-si (KR); Eun Kyung Lee, Seoul (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 0 days.

(21) Appl. No.: 15/293,873

(22) Filed: Oct. 14, 2016

(65) Prior Publication Data

US 2017/0117484 A1    Apr. 27, 2017

(30) Foreign Application Priority Data

Oct. 21, 2015  (KR) .................. 10-2015-0146686

(51) Int. Cl.
| | | |
|---|---|---|
| *H01L 51/00* | (2006.01) | |
| *C07D 517/22* | (2006.01) | |
| *C07D 345/00* | (2006.01) | |
| *H01L 51/05* | (2006.01) | |
| *H01L 51/42* | (2006.01) | |
| *H01L 51/50* | (2006.01) | |

(52) U.S. Cl.
CPC ........ *H01L 51/0071* (2013.01); *C07D 345/00* (2013.01); *C07D 517/22* (2013.01); *H01L 51/0541* (2013.01); *H01L 51/0545* (2013.01); *H01L 51/0558* (2013.01); *H01L 51/42* (2013.01); *H01L 51/5012* (2013.01)

(58) Field of Classification Search
CPC .................................. H01L 51/0071
USPC ....................................... 549/41
See application file for complete search history.

(56) References Cited

U.S. PATENT DOCUMENTS

| | | |
|---|---|---|
| 7,816,673 B2 | 10/2010 | Park et al. |
| 2010/0065826 A1 | 3/2010 | Takimiya et al. |
| 2016/0039962 A1 | 2/2016 | Moon et al. |
| 2016/0226005 A1 | 8/2016 | Park et al. |

FOREIGN PATENT DOCUMENTS

| | | |
|---|---|---|
| EP | 2098527 A1 | 9/2009 |
| EP | 3050887 A1 | 8/2016 |
| JP | 2010/202523 A | 9/2010 |
| KR | 10-1468493 B1 | 12/2014 |
| WO | WO-2008/050726 A1 | 5/2008 |
| WO | WO-2008/084109 A1 | 7/2008 |
| WO | WO-2009/0009790 A1 | 1/2009 |

OTHER PUBLICATIONS

Christian Ruzie et al. "Synthesis of 1,6-, 2,7-, 3,8-, and 4,9-Isomers of Didodecyl[1]benzothieno[3,2-b][1]benzothiophenes". JOC: The Journalof Organic Chemistry. ACS Publications—American Chemical Society. 2013. pp. 7741-7748.

Tatsuya Yamamoto et al. "Facile Synthesis of Highly π-Extended Heteroarenes, Dinaphtho[2,3-b:2',3'-f]chalcogenopheno[3,2-b]chalcogenophenes, and Their Application to Field-Effect Transistors". American Chemical Society. JACS Communications. 2007. pp. 2224-2225.

Kazuo Takimiya et al. "2,7-Diphenyl[1]benzoselenopheno[3,2-b][1]benzoselenophene as a Stable Organic Semiconductor for a High-Performance Field-Effect Transistor". American Chemical Society. JACS Articles. 2006. pp. 3044-3050.

Tue Heesgaard Jepsen et al. "An efficient protocol for synthesizing dibenzodithiapentalenes". Tetrahedron Letters 52. Elsevier Ltd. 2011. pp. 4045-4047.

Extended European Search Report dated Feb. 24, 2017 issued in corresponding European Application No. 16194430.1.

*Primary Examiner* — Taofiq A Solola

(74) *Attorney, Agent, or Firm* — Harness, Dickey & Pierce, P.L.C.

(57) ABSTRACT

An intermediate of a heteroacene compound is represented by Chemical Formula 1.

6 Claims, 3 Drawing Sheets

INTERMEDIATE FOR HETEROACENE COMPOUND AND SYNTHETIC METHOD OF HETEROACENE COMPOUND USING ITS INTERMEDIATE

CROSS-REFERENCE TO RELATED APPLICATION

This application claims priority to and the benefit of Korean Patent Application No. 10-2015-0146686 filed in the Korean Intellectual Property Office on Oct. 21, 2015, the entire contents of which are incorporated herein by reference.

BACKGROUND

1. Field

Example embodiments relate to an intermediate of a heteroacene compound and a synthetic method of a heteroacene compound using the same.

2. Description of the Related Art

In general, flat display devices, e.g., liquid crystal displays or organic electroluminescent displays, are provided with a variety of thin film transistors (TFTs) to drive them. The TFT may include a gate electrode, source/drain electrodes, and a semiconductor layer that may be activated in response to the operation of the gate electrode. The semiconductor layer may include an organic semiconductor material that is controlled by a current between the source electrode and the drain electrode using an applied gate voltage.

Recently, there has been research on a relatively low-molecular-weight organic material or a polymer organic material as an organic semiconductor material to be used for a channel of a thin film transistor. However, because the polymer organic material has lower charge mobility and a higher off-state leakage current, interest in the low-molecular-weight organic material is increasing. As for the relatively low-molecular-weight organic material, a heteroacene compound has higher electron mobility and stability and thus draws attention.

Various methods for manufacturing the heteroacene compound have been suggested, but there is a problem of a relatively high production cost, etc., due to a complicated and relatively long reaction route.

SUMMARY

Example embodiments provide an intermediate of a heteroacene compound capable of manufacturing the heteroacene compound at a relatively low cost through a relatively simple process.

Example embodiments also provide a synthetic method of a heteroacene compound using the intermediate of the heteroacene compound.

Example embodiments also provide an organic thin film and an electronic device including the heteroacene compound.

According to example embodiments, an intermediate of a heteroacene compound is represented by Chemical Formula 1.

[Chemical Formula 1]

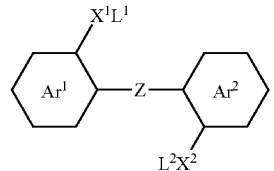

In Chemical Formula 1,
each of $Ar^1$ and $Ar^2$ is independently one of a substituted or unsubstituted aromatic ring, a substituted or unsubstituted heteroaromatic ring, and a condensed ring of the two or more foregoing rings,
Z is one of an ethenylene group and an ethynylene group,
each of $X^1$ and $X^2$ is independently one of O, S, Se, and Te, and
each of $L^1$ and $L^2$ is independently one functional group of Chemical Formula A and B.

[Chemical Formula A]

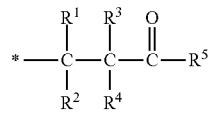

In Chemical Formula A,
each of $R^1$, $R^2$, and $R^3$ is independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group,
$R^4$ is one of hydrogen and a methyl group,
$R^5$ is one of hydrogen, a hydroxy group, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, and an amine group ($NR^xR^y$, wherein each of $R^x$ and $R^y$ is independently one of hydrogen, a $C_1$ to $C_{30}$ alkyl group and a $C_6$ to $C_{30}$ aryl group), and
* indicates a linking position to $X^1$ and $X^2$,

[Chemical Formula B]

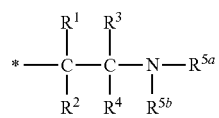

In Chemical Formula B,
each of $R^1$, $R^2$, and $R^3$ is independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group,
$R^4$ is one of hydrogen and a methyl group,
each of $R^{5a}$ and $R^{5b}$ is independently one of hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, and an amine group ($NR^xR^y$, wherein each of $R^x$ and $R^y$ is independently one of hydrogen, a $C_1$ to $C_{30}$ alkyl group, and a $C_6$ to $C_{30}$ aryl group), and

* indicates a linking position to $X^1$ and $X^2$.

In Chemical Formula 1, each of the $Ar^1$ and $Ar^2$ groups may independently be one of phenylene, naphthalenylene, anthracenylene, pyridinylene, and benzothiophenylene.

Each of the $L^1$ and $L^2$ groups may independently be a functional group represented by Chemical Formula A-1.

[Chemical Formula A-1]

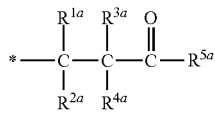

In Chemical Formula A-1, each of $R^{1a}$, $R^{2a}$, and $R^{3a}$ is independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group, $R^{4a}$ is one of hydrogen and a methyl group, $R^{5a}$ is one of a substituted or unsubstituted $C_1$ to $C_{10}$ alkyl group and a substituted or unsubstituted $C_6$ to $C_{10}$ aryl group, and

* indicates a linking position to $X^1$ and $X^2$.

Each of the $L^1$ and $L^2$ groups may independently be a functional group represented by Chemical Formula A-2.

[Chemical Formula A-2]

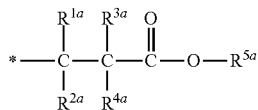

In Chemical Formula A-2, each of $R^{1a}$, $R^{2a}$, and $R^{3a}$ is independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group, $R^{4a}$ is one of hydrogen and a methyl group, $R^{5a}$ is one of hydrogen, a substituted or unsubstituted $C_1$ to $C_{10}$ alkyl group, and a substituted or unsubstituted $C_6$ to $C_{10}$ aryl group, and

* indicates a linking position to $X^1$ and $X^2$.

Each of the $L^1$ and $L^2$ groups may independently be a functional group represented by Chemical Formula A-3.

[Chemical Formula A-3]

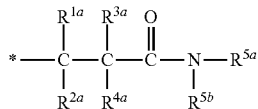

In Chemical Formula A-3, each of $R^{1a}$, $R^{2a}$, and $R^{3a}$ is independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group, $R^{4a}$ is one of hydrogen and a methyl group, each of $R^{5a}$ and $R^{5b}$ is independently one of hydrogen, a substituted or unsubstituted $C_1$ to $C_{10}$ alkyl group, and a substituted or unsubstituted $C_6$ to $C_{10}$ aryl group, and

* indicates a linking position to $X^1$ and $X^2$.

According to example embodiments, an intermediate of a heteroacene compound is represented by one of Chemical Formula 2-1 and Chemical Formula 2-2.

[Chemical Formula 2-1]

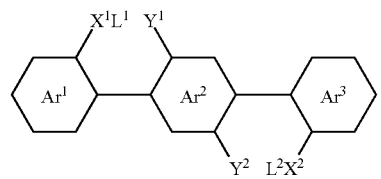

[Chemical Formula 2-2]

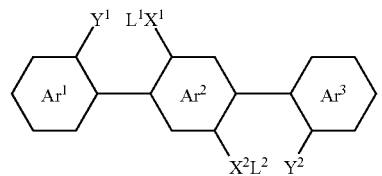

In Chemical Formulae 2-1 and 2-2, each of $Ar^1$, $Ar^2$, and $Ar^a$ is independently one of a substituted or unsubstituted aromatic ring, a substituted or unsubstituted heteroaromatic ring, and a condensed ring of the two or more foregoing rings, each of $X^1$ and $X^2$ is independently one of O, S, Se, and Te, each of $Y^1$ and $Y^2$ is independently one of hydrogen, a halide group, and a sulfonate group, and each of $L^1$ and $L^2$ are independently a functional group represented by one of Chemical Formula A and Chemical Formula B.

[Chemical Formula A]

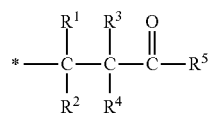

In Chemical Formula A, each of $R^1$, $R^2$, and $R^3$ is independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group, $R^4$ is one of hydrogen and a methyl group, $R^5$ is one of hydrogen, hydroxy group, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, substituted or unsubstituted $C_6$ to $C_{30}$ aryloxy group and amine group ($NR^xR^y$, wherein each of $R^x$ and $R^y$ is independently one of hydrogen, a $C_1$ to $C_{30}$ alkyl group, and a $C_6$ to $C_{30}$ aryl group), and
* indicates a linking position to $X^1$ and $X^2$,

[Chemical Formula B]

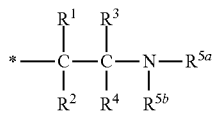

In Chemical Formula B,
each of $R^1$, $R^2$, and $R^3$ is independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group,
$R^4$ is one of hydrogen and a methyl group,
each of $R^{5a}$ and $R^{5b}$ is independently one of hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, and an amine group ($NR^xR^y$, wherein each of $R^x$ and $R^y$ is independently one of hydrogen, a $C_1$ to $C_{30}$ alkyl group, and a $C_6$ to $C_{30}$ aryl group), and
* indicates a linking position to $X^1$ and $X^2$.
In Chemical Formulae 2-1 and 2-2, each of the $Ar^1$, $Ar^2$, and $Ar^a$ groups may independently be one of phenylene, naphthalenylene, anthracenylene, pyridinylene, and benzothiophenylene.
Each of the $L^1$ and $L^2$ groups may independently be a functional group represented by Chemical Formula A-1.

[Chemical Formula A-1]

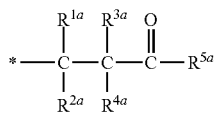

In Chemical Formula A-1,
each of $R^{1a}$, $R^{2a}$, and $R^{3a}$ is independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group,
$R^{4a}$ is one of hydrogen and a methyl group,
$R^{5a}$ is one of a substituted or unsubstituted $C_1$ to $C_{10}$ alkyl group and a substituted or unsubstituted $C_6$ to $C_{10}$ aryl group, and
* indicates a linking position to $X^1$ and $X^2$.
Each of the $L^1$ and $L^2$ groups may independently be a functional group represented by Chemical Formula A-2.

[Chemical Formula A-2]

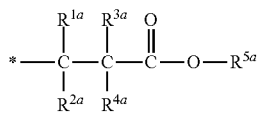

In Chemical Formula A-2,
each of $R^{1a}$, $R^{2a}$, and $R^{3a}$ is independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group,
$R^{4a}$ is one of hydrogen and a methyl group,
$R^{5a}$ is one of a substituted or unsubstituted $C_1$ to $C_{10}$ alkyl group and a substituted or unsubstituted $C_6$ to $C_{10}$ aryl group, and
* indicates a linking position to $X^1$ and $X^2$.
Each of the $L^1$ and $L^2$ groups may independently be a functional group represented by Chemical Formula A-3.

Chemical Formula A-3]

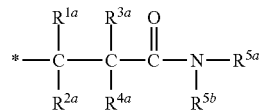

In Chemical Formula A-3,
each of $R^{1a}$, $R^{2a}$, and $R^{3a}$ is independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group,
$R^{4a}$ is one of hydrogen and a methyl group,
each of $R^{5a}$ and $R^{5b}$ is independently one of a substituted or unsubstituted $C_1$ to $C_{10}$ alkyl group and a substituted or unsubstituted $C_6$ to $C_{10}$ aryl group, and
* indicates a linking position to $X^1$ and $X^2$.
The sulfonate group may be represented by Chemical Formula C.

[Chemical Formula C]

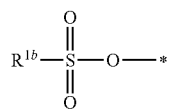

In Chemical Formula C,
$R^{1b}$ is one of a $C_1$ to $C_{10}$ alkyl group, a $C_1$ to $C_{10}$ haloalkyl group, and a $C_6$ to $C_{10}$ aryl group, and
* indicates a linking position to one of $Ar^2$ in Chemical Formula 2-1 and a linking position to $Ar^1$ and $Ar^3$ in Chemical Formula 2-2.
The intermediate of the heteroacene compound represented by Chemical Formula 1 may be a compound represented by Chemical Formula 3-1.

[Chemical Formula 3-1]

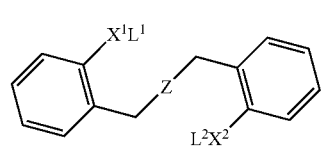

(1)

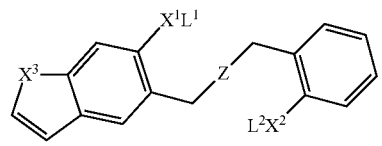

(2)

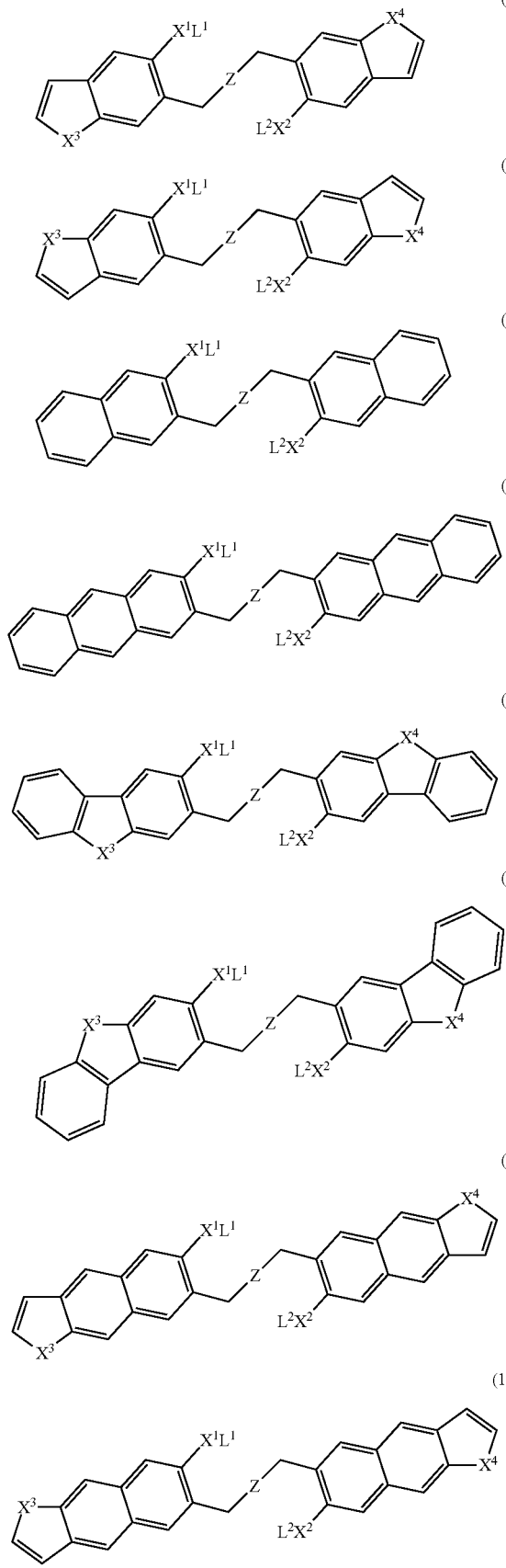

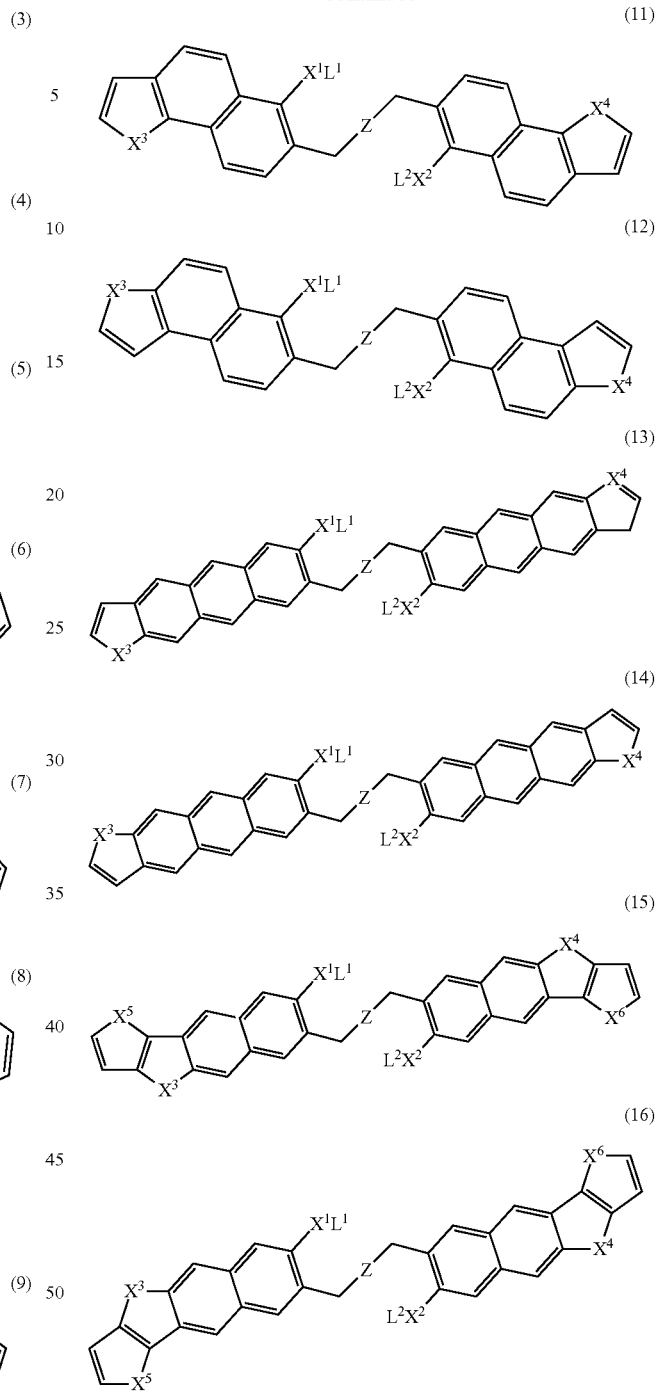

In Chemical Formula 3-1,

Z is one of an ethenylene group and an ethynylene group, each of $X^1$ and $X^2$ is independently one of O, S, Se, and Te, each of $L^1$ and $L^2$ is independently the functional group represented by Chemical Formula A or Chemical Formula B, and each of $X^3$, $X^4$, $X^5$, and $X^6$ is independently one of O, S, Se, Te, N—$R^x$, and $C(R^y)$=$C(R^z)$, wherein $R^x$, $R^y$, and $R^z$ is independently one of hydrogen and a linear or branched $C_1$ to $C_{10}$ alkyl group.

The intermediate of the heteroacene compound represented by Chemical Formula 2-1 may be a compound of Chemical Formula 4-1 and the intermediate of the heteroacene compound represented by Chemical Formula 2-2 may be a compound of Chemical Formula 4-2.
[Chemical Formula 4-1]
(17)
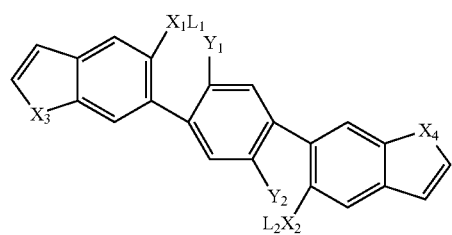
(18)
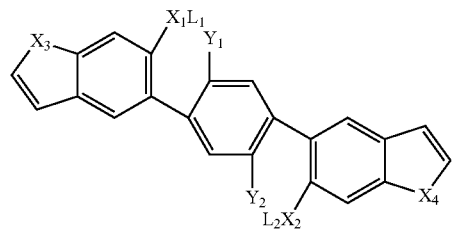
(19)
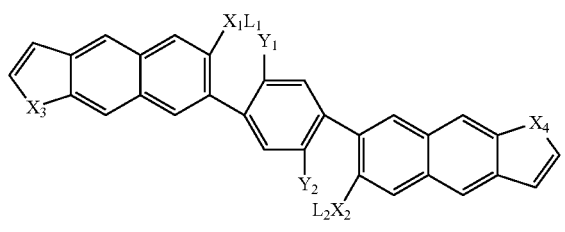
(20)
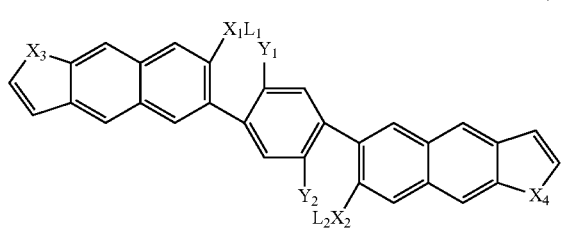
(21)
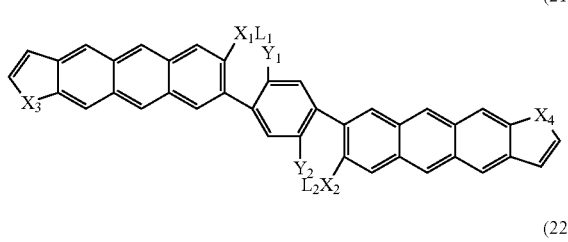
(22)
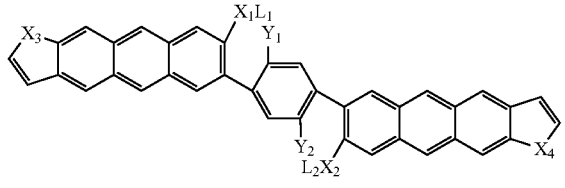
(23)
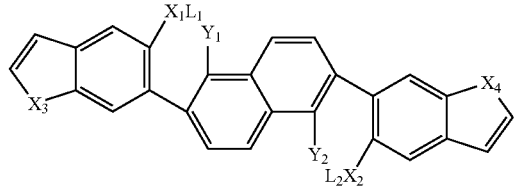
(24)
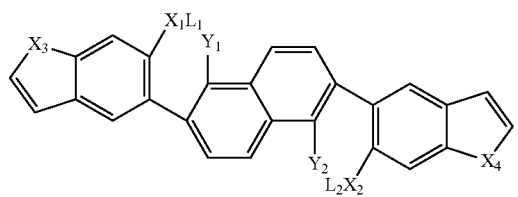
[Chemical Formula 4-2]
(25)
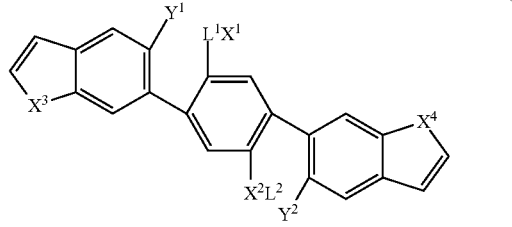
(26)
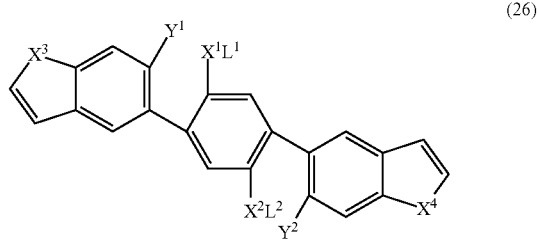
(27)
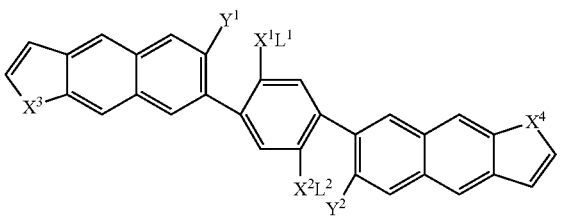
(28)
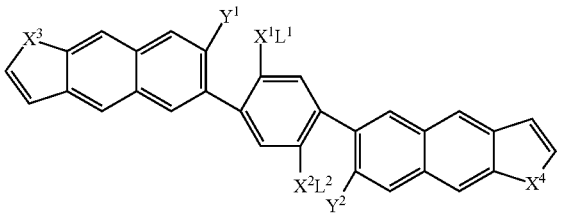

(29)

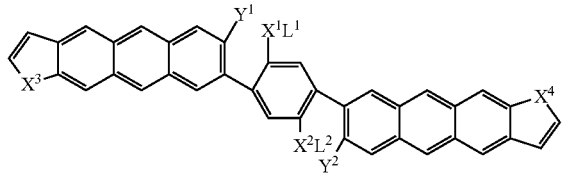

(30)

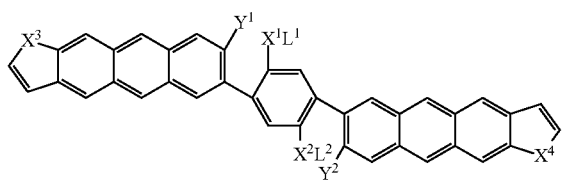

(31)

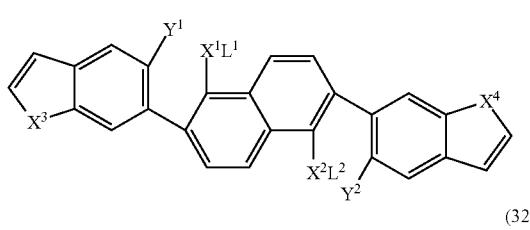

(32)

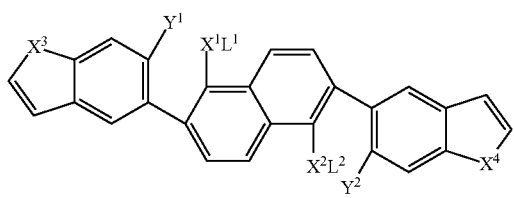

In Chemical Formulae 4-1 and 4-2, each of $X^1$ and $X^2$ is independently one of O, S, Se, and Te, each of $L^1$ and $L^2$ are independently the functional group represented by Chemical Formula A or B, each of $X^3$ and $X^4$ is independently one of O, S, Se, Te, N—$R^x$, and $C(R^y)$=$C(R^z)$, wherein each of $R^x$, $R^y$, and $R^z$ is independently one of hydrogen and a linear or branched $C_1$ to $C_{10}$ alkyl group.

In Chemical Formulae 3-1, 4-1, and 4-2, a hydrogen of each aromatic ring may be replaced by a substituent, for example, one of a $C_1$ to $C_{30}$ linear or branched alkyl group, a substituted or unsubstituted $C_6$ to $C_{30}$ aryl group, a substituted or unsubstituted $C_2$ to $C_{30}$ heteroaryl group, a substituted or unsubstituted C7 to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted C5 to $C_{30}$ cycloalkyl group, and a substituted or unsubstituted $C_2$ to $C_{30}$ heterocycloalkyl group.

According to example embodiments, a synthetic method of a heteroacene compound includes forming a chalogenophene ring by reacting an intermediate of a heteroacene compound represented by one of Chemical Formulae 1, 2-1, and 2-2 with a base material. The reaction uses the intermediate of a heteroacene compound represented by one of Chemical Formula 1, 2-1, and 2-2 and thus may be performed under various process conditions and expand a process margin.

The base material may be one of metal alkoxide, metal amine, phosphine compound, and a combination thereof.

The metal alkoxide may be represented by Chemical Formula 5.

$$(RO)_nM \quad \text{[Chemical Formula 5]}$$

In Chemical Formula 5,

R is a linear or branched $C_1$ to $C_{10}$ alkyl group, M is one of an alkali metal and an alkaline-earth metal, and n is an integer of 1 or 2.

The metal amine may be represented by Chemical Formula 6.

$$M(NRR')_n \quad \text{[Chemical Formula 6]}$$

In Chemical Formula 6, each of R and R' is a linear or branched $C_1$ to $C_{10}$ alkyl group, M is one of an alkali metal and an alkaline-earth metal, and n is an integer of 1 or 2.

The reaction between the intermediate and the base material may be performed in one of a hydrocarbon-based solvent, an ether-based solvent, an amide based solvent, a sulfoxide based solvent, and a combination thereof.

The hydrocarbon-based solvent may be one of benzene, toluene, xylene, and a combination thereof, the ether-based solvent may be one of dialkylether (wherein the alkyl is a $C_1$ to $C_{10}$ linear or branched alkyl), e.g., diethylether, dibutylether, tetrahydrofuran, 2-methyl tetrahydrofuran, dimethoxyethane, dioxane, diglyme, tetaglyme and a combination thereof, the amide-based solvent may be one of dimethyl formamide, dimethyl acetamide, and a combination thereof, and the sulfoxide-based solvent may be dimethyl sulfoxide.

According to example embodiments, a heteroacene compound is synthesized by the synthetic method of example embodiments.

According to example embodiments, an organic thin film and an electronic device include the heteroacene compound of example embodiments.

The electronic device may be one of a transistor, an organic light emitting diode (OLED), a photovoltaic device, a solar cell, a laser device, a memory device, and a sensor.

According to example embodiments, a transistor includes a gate electrode on a substrate, an insulation layer covering the gate electrode, a source electrode and a drain electrode on the insulation layer, and an active layer between the source electrode and the drain electrode, the active layer including the heteroacene compound of example embodiments.

According to example embodiments, a transistor includes a source electrode and a drain electrode on a substrate, an active layer between the source electrode and the drain electrode, the active layer including the heteroacene compound of example embodiments, an insulation layer covering the source electrode, the drain electrode, and the active layer, and a gate electrode on the insulation layer.

According to example embodiments, an organic light emitting diode (OLED) apparatus includes a first electrode on a substrate, a first emission layer on the first electrode, a buffer layer on the first emission layer, a middle electrode on the buffer layer, a second emission layer on the middle electrode, and a second electrode on the second emission layer, wherein at least one of the first and second emission layers include the heteroacene compound of example embodiments.

According to example embodiments, a solar cell includes a first electrode and a second electrode spaced apart from each other and a photoactive layer between the first electrode and the second electrode, the photoactive layer including the heteroacene compound of example embodiments.

According to example embodiments, a sensor includes at least one electrode configured to output a signal to a processor, the at least one electrode including the heteroacene compound of example embodiments.

DETAILED DESCRIPTION

Figure 1:
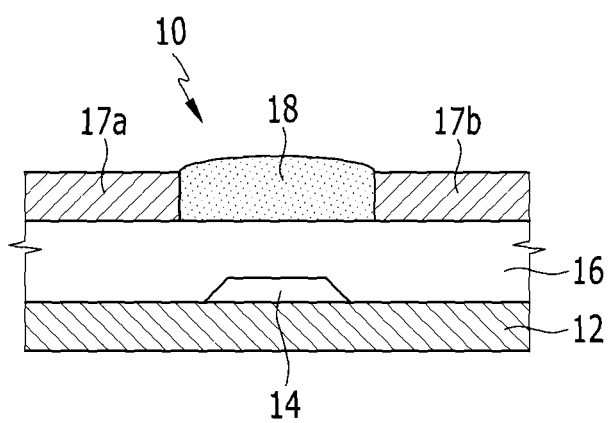
FIG. 1 is a schematic cross-sectional view showing a transistor according to example embodiments.

The present disclosure will be described more fully hereinafter with reference to the accompanying drawings, in which example embodiments of this disclosure are shown. However, this disclosure may be embodied in many different forms and is not construed as limited to the example embodiments set forth herein.

In the drawings, the thickness of layers, films, panels, regions, etc., are exaggerated for clarity.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," etc.) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, the term "combination thereof" refers to a mutually linked substituents, a mixture, a stacked structure, etc.

As used herein, when a definition is not otherwise provided, the prefix "hetero" may refer to a group that includes 1 to 4 heteroatoms, each independently one of N, O, S, Si, and P. The total number of ring members may be 3 to 10. If multiple rings are present, each ring is independently aromatic, saturated, or partially unsaturated, and multiple rings, if present, may be fused, pendant, spirocyclic, or a combination thereof. Heterocycloalkyl groups include at least one non-aromatic ring that contains a heteroatom ring member. Heteroaryl groups include at least one aromatic ring that contains a heteroatom ring member. Non-aromatic and/or carbocyclic rings may also be present in a heteroaryl group, provided that at least one ring is both aromatic and contains a ring member that is a heteroatom.

As used herein, when a definition is not otherwise provided, the term "alkyl group" may be a linear or branched saturated monovalent hydrocarbon group (e.g., a methyl group, an ethyl group, a propyl group, an isobutyl group, a sec-butyl group, a tert-butyl group, a pentyl group, an iso-amyl group, a hexyl group, etc).

The term "aryl group" may refer to a monovalent functional group formed by the removal of one hydrogen atom from a ring of an arene, e.g., phenyl or naphthyl. The arene may refer to a hydrocarbon having an aromatic ring, and includes monocyclic and polycyclic hydrocarbons, wherein the additional ring(s) of the polycyclic hydrocarbon may be aromatic or nonaromatic.

The "arylalkyl group" may refer to an aryl group where at least one hydrogen atom is substituted with a lower alkylene, e.g., methylene, ethylene, propylene, etc. For example, the "arylalkyl group" may be a benzyl group or a phenylethyl group.

The term "cycloalkyl group" may refer to a monovalent functional group having one or more saturated rings in which all ring members are carbon, e.g., a cyclopentyl group and a cyclohexyl group.

The term "heteroarylalkyl group" may refer to the alkyl group defined above where at least one hydrogen atom is substituted with a heteroaryl group.

The term "alkylheteroaryl group" may refer to the heteroaryl group defined above, where at least one hydrogen atom is substituted with an alkyl group.

As used herein, when a definition is not otherwise provided, the term "aromatic ring" refers to a functional group in which all atoms in the cyclic functional group have a p-orbital, and wherein these p-orbitals are conjugated. For example, the aromatic ring may be a $C_6$ to $C_{20}$ aryl group.

The term "heteroaromatic ring" refers to the aromatic ring including 1 to 4 heteroatoms selected from N, O, S, Se, Si and P per one ring.

As used herein, when a definition is not otherwise provided, the term "substituted" means that a compound or group is substituted with at least one substituent independently selected from a halogen (—F, —Cl, —Br, or —I), a $C_1$ to $C_{30}$ linear or branched alkyl group, for example, a $C_1$ to $C_{10}$ linear or branched alkyl group, a $C_2$ to $C_{30}$ linear or branched alkenyl group, for example, a $C_2$ to $C_{10}$ linear or branched alkenyl group, a $C_2$ to $C_{30}$ linear or branched alkynyl group, for example, a $C_2$ to $C_{10}$ linear or branched alkynyl group, a $C_6$ to $C_{30}$ aryl group, for example, a $C_6$ to $C_{12}$ aryl group, a $C_2$ to $C_{30}$ heteroaryl group, for example, a $C_2$ to $C_{12}$ heteroaryl group, a $C_3$ to $C_{30}$ cycloalkyl group, a $C_1$ to $C_{20}$ fluoroalkyl group, a $C_1$ to $C_{20}$ perfluoroalkyl group ($C_nF_{2n+i}$), a $C_1$ to $C_{30}$ linear or branched alkoxy group, a $C_3$ to $C_{30}$ cycloalkoxy group, a $C_2$ to $C_{30}$ linear or branched alkoxyalkyl group, a $C_4$ to $C_{30}$ cycloalkoxyalkyl group, a cyano group, an amino group (—NRR', wherein each of R and R' is independently one of hydrogen or a $C_1$ to $C_{10}$ alkyl group), an amidino group (—C(=NH)NH$_2$), a nitro group (—NO$_2$), an amide group (—C(=O)NHR, wherein R is hydrogen or a $C_1$ to $C_{10}$ alkyl group), an aldehyde group (—C(=O)H), a hydroxy group (—OH), a sulfonyl group (—S(=O)$_2$R, wherein R is independently hydrogen or a $C_1$ to $C_{10}$ alkyl group), and a carbamate group (—NHC(=O)OR, wherein R is a $C_1$ to $C_{10}$ alkyl group), instead of hydrogen of the group or the compound, provided that the substituted atom's normal valence is not exceeded.

According to example embodiments, an intermediate of a heteroacene compound is represented by Chemical Formula 1.

[Chemical Formula 1]

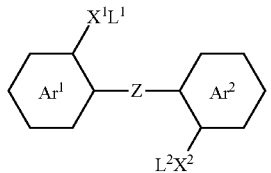

In Chemical Formula 1, each of $Ar^1$ and $Ar^2$ is independently one of a substituted or unsubstituted aromatic ring, a substituted or unsubstituted heteroaromatic ring, and a condensed ring of the two or more foregoing rings, Z is one of an ethenylene group (—CH=CH—) and an ethynylene group (—C≡C—), each of $X^1$ and $X^2$ is independently one of O, S, Se, and Te, and each of $L^1$ and $L^2$ is independently one of functional groups of Chemical Formula A and Chemical Formula B.

[Chemical Formula A]

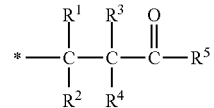

In Chemical Formula A, each of $R^1$, $R^2$, and $R^3$ is independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group, $R^4$ is one of hydrogen and a methyl group, $R^5$ is one of hydrogen, a hydroxy group, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, substituted or unsubstituted $C_6$ to $C_{30}$ aryloxy group and amine group (NR$^x$R$^y$, wherein each of R$^x$ and R$^y$ is independently one of hydrogen, a $C_1$ to $C_{30}$ alkyl group, and a $C_6$ to $C_{30}$ aryl group), and

* indicates a linking position to $X^1$ and $X^2$,

[Chemical Formula B]

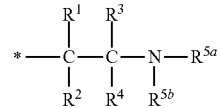

wherein, in Chemical Formula B, each of $R^1$, $R^2$, and $R^3$ is independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group, $R^4$ is one of hydrogen and a methyl group, each of $R^{5a}$ and $R^{5b}$ is independently one of hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, and an amine group (NR$^x$R$^y$, wherein each of R$^x$ and R$^y$ is independently one of hydrogen, a $C_1$ to $C_{30}$ alkyl group, and a $C_6$ to $C_{30}$ aryl group), and

* indicates a linking position to $X^1$ and $X^2$.

In Chemical Formula 1, each of $Ar^1$ and $Ar^2$ may independently be one of phenylene, naphthalenylene, anthracenylene, pyridinylene, and benzothiophenylene.

In example embodiments, at least one of $R^3$ and $R^4$ of Chemical Formulae A and B may be hydrogen.

In Chemical Formula 1, each of $X^1L^1$ and $X^2L^2$ reacts with Z by a ring closure reaction to provide an $X^1$-containing heteroaromatic ring and an $X^2$-containing heteroaromatic ring. For example, when each of $X^1$ and $X^2$ is S and Z is an ethenylene group or an ethynylene group, a thienothiophene may be provided by a ring closure reaction.

$L^1$ and $L^2$ may independently be a functional group represented by Chemical Formula A-1.

[Chemical Formula A-1]

$$*-\underset{\underset{R^{2a}}{|}}{\overset{\overset{R^{1a}}{|}}{C}}-\underset{\underset{R^{4a}}{|}}{\overset{\overset{R^{3a}}{|}}{C}}-\overset{\overset{O}{\|}}{C}-R^{5a}$$

In Chemical Formula A-1, $R^{1a}$, $R^{2a}$, and $R^{3a}$ are independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group, $R^{4a}$ is one of hydrogen and a methyl group, $R^{5a}$ is one of a substituted or unsubstituted $C_1$ to $C_{10}$ alkyl group and a substituted or unsubstituted $C_6$ to $C_{10}$ aryl group, and

* indicates a linking position to $X^1$ and $X^2$.

In example embodiments, at least one of $R^{3a}$ and $R^{4a}$ of Chemical Formula A-1 may be hydrogen.

The $L^1$ and $L^2$ may independently be a functional group represented by Chemical Formula A-2.

[Chemical Formula A-2]

$$*-\underset{\underset{R^{2a}}{|}}{\overset{\overset{R^{1a}}{|}}{C}}-\underset{\underset{R^{4a}}{|}}{\overset{\overset{R^{3a}}{|}}{C}}-\overset{\overset{O}{\|}}{C}-O-R^{5a}$$

In Chemical Formula A-2, $R^{1a}$, $R^{2a}$, and $R^{3a}$ are independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group, $R^{4a}$ is one of hydrogen and a methyl group, $R^{5a}$ is one of a substituted or unsubstituted $C_1$ to $C_{10}$ alkyl group and a substituted or unsubstituted $C_6$ to $C_{10}$ aryl group, and

* indicates a linking position to $X^1$ and $X^2$.

In example embodiments, at least one of $R^{3a}$ and $R^{4a}$ of Chemical Formula A-2 may be hydrogen.

The $L^1$ and $L^2$ may independently be a functional group represented by Chemical Formula A-3.

[Chemical Formula A-3]

$$*-\underset{\underset{R^{2a}}{|}}{\overset{\overset{R^{1a}}{|}}{C}}-\underset{\underset{R^{4a}}{|}}{\overset{\overset{R^{3a}}{|}}{C}}-\overset{\overset{O}{\|}}{C}-\underset{\underset{R^{5b}}{|}}{N}-R^{5a}$$

In Chemical Formula A-3, each of $R^{1a}$, $R^{2a}$, and $R^{3a}$ are independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group, $R^{4a}$ is one of hydrogen and a methyl group, each of $R^{5a}$ and $R^{5b}$ are independently one of a substituted or unsubstituted $C_1$ to $C_{10}$ alkyl group and a substituted or unsubstituted $C_6$ to $C_{10}$ aryl group, and

* indicates a linking position to $X^1$ and $X^2$.

In example embodiments, at least either one of $R^{3a}$ and $R^{4a}$ in Chemical Formula A-3 may be hydrogen.

According to example embodiments, the intermediate of a heteroacene compound may be represented by one of Chemical Formula 2-1 and 2-2.

[Chemical Formula 2-1]

$$\text{Ar}^1 - \overset{X^1 L^1 \ Y^1}{\text{Ar}^2} - \underset{Y^2 \ L^2 X^2}{\text{Ar}^3}$$

[Chemical Formula 2-2]

$$\text{Ar}^1 - \overset{Y^1 \ L^1 X^1}{\text{Ar}^2} - \underset{X^2 L^2 \ Y^2}{\text{Ar}^3}$$

In Chemical Formula 2-1 and Chemical Formula 2-2, each of $\text{Ar}^1$, $\text{Ar}^2$, and $\text{Ar}^a$ are independently one of a substituted or unsubstituted aromatic ring, a substituted or unsubstituted heteroaromatic ring, and a condensed ring of the two or more foregoing rings, each of $X^1$ and $X^2$ are independently one of O, S, Se, and Te, each of $Y^1$ and $Y^2$ are independently one of hydrogen, a halide group, and a sulfonate group, and each of $L^1$ and $L^2$ are independently one of functional groups of Chemical Formula A and Chemical Formula B,

[Chemical Formula A]

$$*-\underset{\underset{R^{2}}{|}}{\overset{\overset{R^{1}}{|}}{C}}-\underset{\underset{R^{4}}{|}}{\overset{\overset{R^{3}}{|}}{C}}-\overset{\overset{O}{\|}}{C}-R^{5}$$

wherein, in Chemical Formula A, each of $R^1$, $R^2$, and $R^3$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group, $R^4$ is one of hydrogen and a methyl group, $R^5$ is one of hydrogen, hydroxy group, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, substituted or unsubstituted $C_6$ to $C_{30}$ aryloxy group and amine group ($NR^xR^y$, wherein each of $R^x$ and $R^y$ is independently one of hydrogen, a $C_1$ to $C_{30}$ alkyl group, and a $C_6$ to $C_{30}$ aryl group), and

* indicates a position linked to $X^1$ and $X^2$,

[Chemical Formula B]

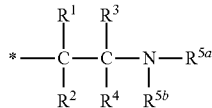

wherein, in Chemical Formula B, each of $R^1$, $R^2$, and $R^3$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group, $R^4$ is one of hydrogen and a methyl group, each of $R^{5a}$ and $R^{5b}$ are independently one of hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, and an amine group ($NR^xR^y$, wherein each of $R^x$ and $R^y$ is independently one of hydrogen, a $C_1$ to $C_{30}$ alkyl group, and a $C_6$ to $C_{30}$ aryl group), and

* indicates a position linked to $X^1$ and $X^2$.

In Chemical Formulae 2-1 and 2-2, each of $Ar^1$, $Ar^2$, and $Ar^3$ may be independently one of phenylene, naphthalenylene, anthracenylene, pyridinylene, and benzothiophenylene.

Each of $L^1$ and $L^2$ may be independently a functional group represented by Chemical Formula A-1.

[Chemical Formula A-1]

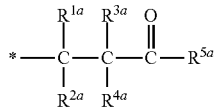

In Chemical Formula A-1, each of $R^{1a}$, $R^{2a}$, and $R^{3a}$ are independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group, $R^{4a}$ is one of hydrogen and a methyl group, $R^{5a}$ is one of a substituted or unsubstituted $C_1$ to $C_{10}$ alkyl group and a substituted or unsubstituted $C_6$ to $C_{10}$ aryl group, and

* indicates a linking position to $X^1$ and $X^2$.

In example embodiments, at least one of $R^{3a}$ and $R^{4a}$ of Chemical Formula A-1 may be hydrogen.

The $L^1$ and $L^2$ may independently be a functional group represented by Chemical Formula A-2.

[Chemical Formula A-2]

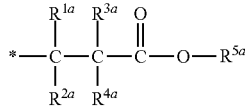

In Chemical Formula A-2, each of $R^{1a}$, $R^{2a}$, and $R^{3a}$ is independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group, $R^{4a}$ is one of hydrogen and a methyl group, $R^{5a}$ is one of a substituted or unsubstituted $C_1$ to $C_{10}$ alkyl group and a substituted or unsubstituted $C_6$ to $C_{10}$ aryl group, and

* indicates a linking position to $X^1$ and $X^2$.

In example embodiments, at least one of $R^{3a}$ and $R^{4a}$ of Chemical Formula A-2 may be hydrogen.

The $L^1$ and $L^2$ may independently be a functional group represented by Chemical Formula A-3.

[Chemical Formula A-3]

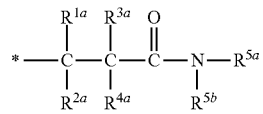

In Chemical Formula A-3, each of $R^{1a}$, $R^{2a}$, and $R^{3a}$ is independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group, $R^{4a}$ is one of hydrogen and a methyl group, each of $R^{5a}$ and $R^{5b}$ is independently one of a substituted or unsubstituted $C_1$ to $C_{10}$ alkyl group and a substituted or unsubstituted $C_6$ to $C_{10}$ aryl group, and

* indicates a linking position to $X^1$ and $X^2$.

In example embodiments, at least one of $R^{1a}$ and $R^{4a}$ of Chemical Formula A-3 may be hydrogen.

Each of $Y^1$ and $Y^2$ may be a halide group, e.g., a fluoro group or a chloro group.

Each of $Y^1$ and $Y^2$ may be the sulfonate group and may be represented by Chemical Formula C.

[Chemical Formula C]

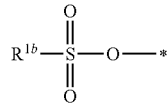

In Chemical Formula C, $R^{1b}$ is one of a $C_1$ to $C_{10}$ alkyl group, a $C_1$ to $C_{10}$ haloalkyl group, and a $C_6$ to $C_{10}$ aryl group, and * indicates a linking position to one of $Ar^2$ in Chemical Formula 2-1 and a linking position to $Ar^1$ and $Ar^3$ in Chemical Formula 2-2. The haloalkyl group may be a fluoro alkyl group, for example, a trifluoromethyl group.

The intermediate of the heteroacene compound represented by Chemical Formula 1 may be a compound of Chemical Formula 3-1.

[Chemical Formula 3-1]

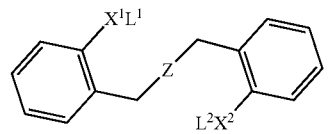

(1)

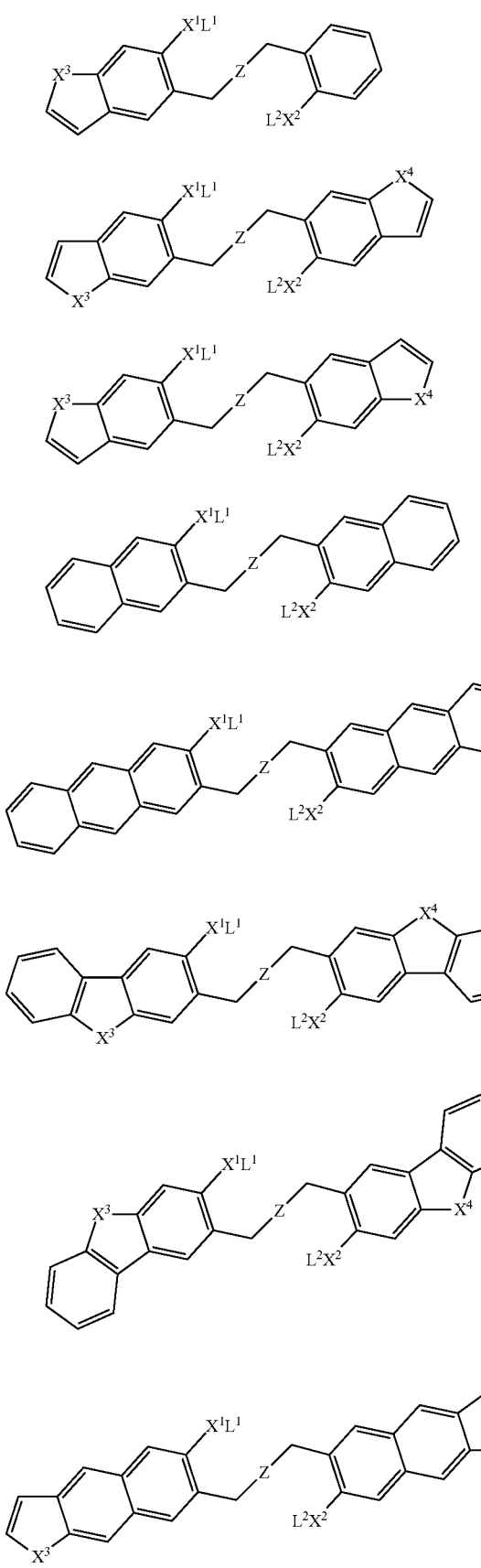
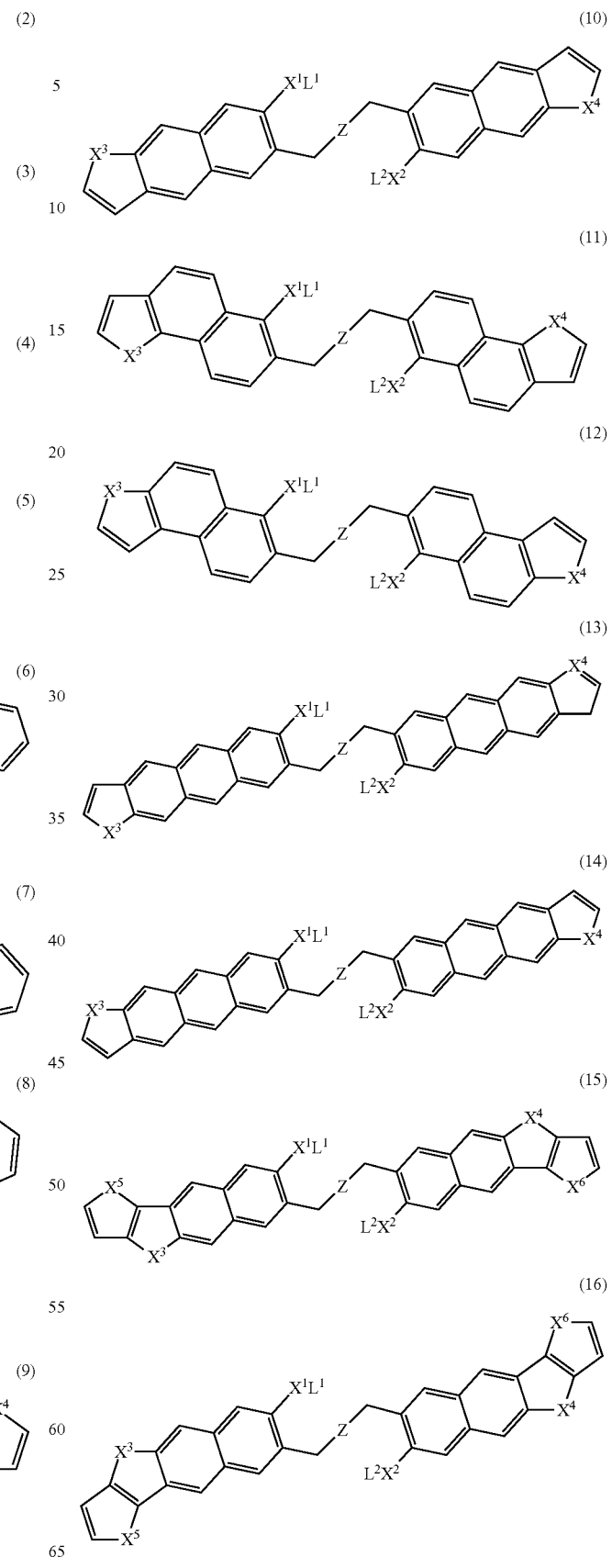

In Chemical Formula 3-1,

Z is one of an ethenylene group and an ethynylene group, each of $X^1$ and $X^2$ is independently one of O, S, Se, and Te, each of $L^1$ and $L^2$ is independently the functional group represented by Chemical Formula A or Chemical Formula B, each of $X^3$, $X^4$, $X^5$, and $X^6$ is independently one of O, S, Se, Te, N—$R^x$, and $C(R^y)$=$C(R^z)$, wherein $R^x$, $R^y$, and $R^z$ are independently one of hydrogen and a linear or branched $C_1$ to $C_{10}$ alkyl group.

In Chemical Formula 3-1, each of $X^1L^1$ and $X^2L^2$ reacts with Z by a ring closure reaction to provide a chalogenophene ring.

The intermediate of a heteroacene compound represented by Chemical Formula 2-1 may be a compound of one of Chemical Formula 4-1 and the intermediate of a heteroacene compound represented by Chemical Formula 2-1 may be a compound of Chemical Formula 4-2.

[Chemical Formula 4-1]

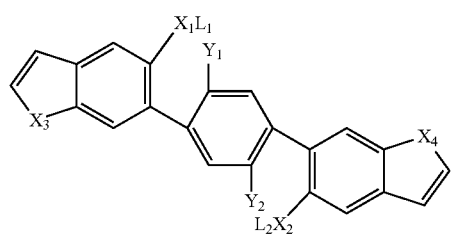
(17)

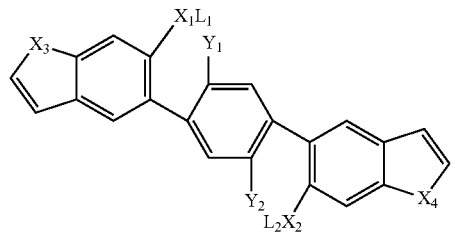
(18)

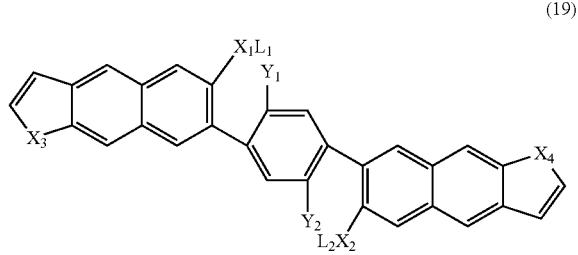
(19)

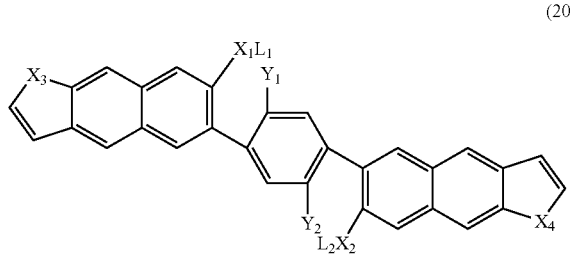
(20)

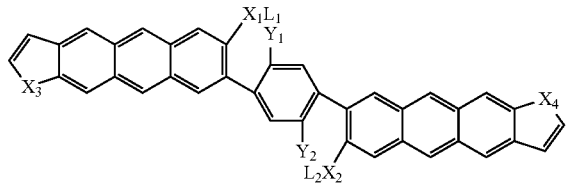
(21)

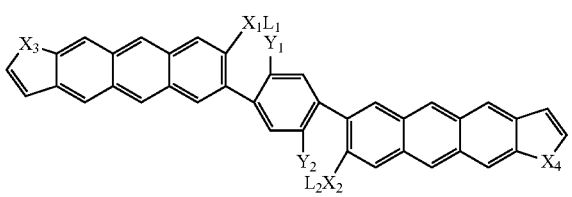
(22)

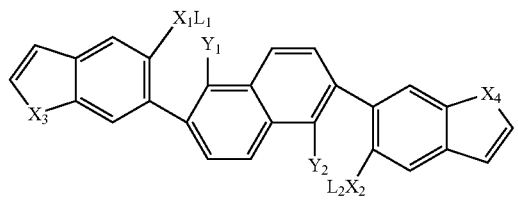
(23)

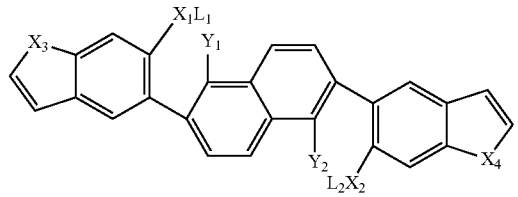
(24)

In Chemical Formula 4-1, each of $X^1$ and $X^2$ is independently one of O, S, Se, and Te, each of $L^1$ and $L^2$ is independently the functional group represented by Chemical Formula A or B, each of $X^3$ and $X^4$ is independently one of O, S, Se, Te, NN—$R^x$, and $C(R^y)$=$C(R^z)$, wherein $R^x$, $R^y$, and $R^z$ are independently one of hydrogen and linear or branched $C_1$ to $C_{10}$ alkyl group, and each of $Y^1$ and $Y^2$ is independently one of hydrogen, a halide group, and a sulfonate group.

[Chemical Formula 4-2]

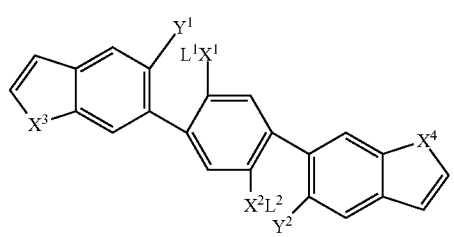
(25)

(26)
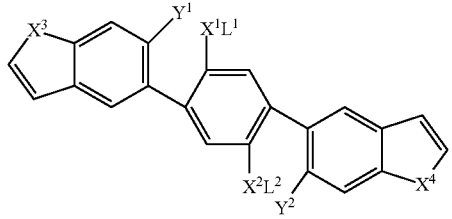

(27)
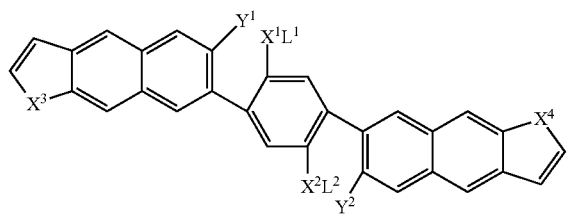

(28)
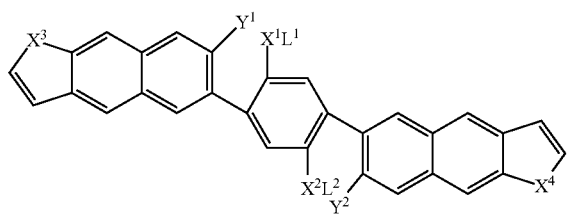

(29)
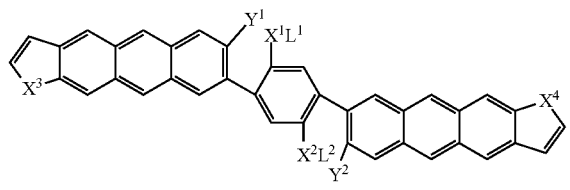

(30)
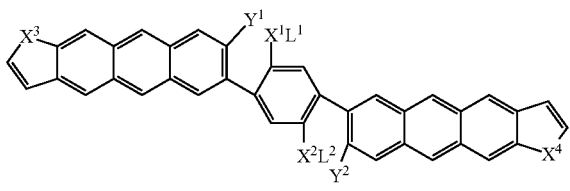

(31)
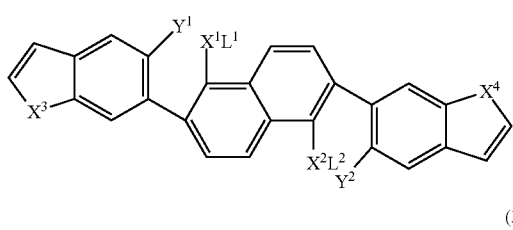

(32)
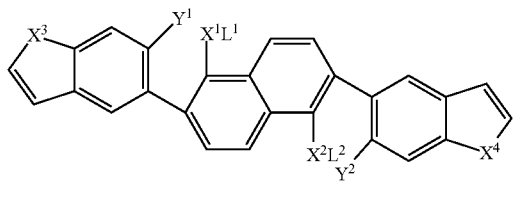

In Chemical Formula 4-2, each of $X^1$ and $X^2$ is independently one of O, S, Se, and Te, each of $L^1$ and $L^2$ are independently the functional group represented by Chemical Formula A or B, each of $X^3$ and $X^4$ is independently one of O, S, Se, Te, NN—$R^x$, and $C(R^y)\!\!=\!\!C(R^z)$, wherein $R^x$, $R^y$, and $R^z$ are independently one of hydrogen and linear or branched $C_1$ to $C_{10}$ alkyl group, each of $Y^1$ and $Y^2$ is independently one of hydrogen, a halide group, and a sulfonate group.

In Chemical Formulae 4-1 and 4-2, each of $X^1L^1$ and $X^2L^2$ reacts with $Y^1$ and $Y^2$ by a ring closure reaction to provide a chalogenophene ring.

In Chemical Formulae 3-1, 4-1, and 4-2, hydrogen of each aromatic ring may be replaced by a substituent, for example, a $C_1$ to $C_{30}$ linear or branched alkyl group, a substituted or unsubstituted $C_6$ to $C_{30}$ aryl group, a substituted or unsubstituted $C_2$ to $C_{30}$ heteroaryl group, a substituted or unsubstituted C7 to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted C5 to $C_{30}$ cycloalkyl group, and a substituted or unsubstituted $C_2$ to $C_{30}$ heterocycloalkyl group.

Example embodiments provide a synthetic method of a heteroacene compound including processes of reacting an intermediate of a heteroacene compound represented by one of Chemical Formula 1, Chemical Formula 2-1, and Chemical Formula 2-2 with a base material by a ring closure reaction to provide a chalogenophene ring.

The synthetic method is a process of reacting the intermediate with a base material and consists of simple steps. In addition, because the base material is more easily removed, a product may be more easily purified.

The synthetic method may be performed at a relatively low temperature, for example, in a range of about 40° C. to about 200° C., for example, about 40° C. to about 100° C.

The base material may be one of metal alkoxide, metal amine, phosphine compound, and a combination thereof.

The metal alkoxide may be represented by Chemical Formula 5.

$(RO)_nM$  [Chemical Formula 5]

In Chemical Formula 5,

R is a linear or branched $C_1$ to $C_{10}$ alkyl group, M is an alkali metal or an alkaline-earth metal, and n is determined by a valence of M, and an integer of 1 or 2. Examples of the M may be one of Li, Na, K, Rb, Cs, Ca, and Mg.

The metal alkoxide may be tertiary alkoxide, e.g., potassium t-butoxide.

The metal amine may be represented by Chemical Formula 6.

$M(NRR')_n$  [Chemical Formula 6]

In Chemical Formula 6, each of R and R' is a linear or branched $C_1$ to $C_{10}$ alkyl group, M is an alkali metal or an alkaline-earth metal, and n is determined by a valence of M, and is an integer of 1 or 2.

Examples of the M may be one of Li, Na, K, Rb, Cs, Ca, and Mg.

The phosphine compound may be alkyl phosphine, aryl phosphine, a phosphazene compound, etc. The alkyl may be a $C_1$ to $C_{10}$ linear or branched alkyl and the aryl may be a $C_6$ to $C_{10}$ aryl.

The phosphazene compound may be hexafluorocyclotriphosphazene, 1-tert-butyl-4,4,4-tris(dimethylamino)-2,2-bis[tris(dimethylamino)-phosphoranylidenamino]-2λ5,4λ5-catenadi(phosphazene), 1-ethyl-2,2,4,4,4-pentakis(dimethylamino)-2λ5,4λ5-catenadi(phosphazene), tetramethyl(tris(dimethylamino)phosphoranylidene)phosphorictriamid-Et-imin, tert-octylimino-tris(dimethylamino)phosphorene, etc.

The base material may be used in an amount of about 100 mol to about 1000 mol based on 100 mol of the intermediate compound. Within the range, the ring closure reaction may be effectively performed.

The ring closure reaction may be performed in a solvent selected from a hydrocarbon-based solvent, an ether-based solvent, an amide based solvent, a sulfoxide based solvent, and a combination thereof.

The hydrocarbon-based solvent may be one of benzene, toluene, xylene, and a combination thereof, the ether-based solvent may be one of dialkylether (wherein alkyl is a $C_1$ to $C_{10}$ linear or branched alkyl), e.g., diethylether, dibutylether, tetrahydrofuran, 2-methyl tetrahydrofuran, dimethoxyethane, dioxane, diglyme, tetaglyme and a combination thereof, the amide-based solvent may be one of dimethyl formamide, dimethyl acetamide, and a combination thereof, and the sulfoxide-based solvent may be dimethyl sulfoxide.

The heteroacene compound synthesized through the ring closure reaction of the intermediate of a heteroacene compound has a structure that 4 or more, for example, 5 or more aromatic rings and hetero aromatic rings are fused. Because of this compact planar-type molecular structure, the heteroacene compound has an advantage in packing and stacking molecules as well as a uniform and stable oxidation potential and thus exhibits high charge mobility, when actually applied to a device, and may be used as a semiconductor material, an electron transport material, etc.

The heteroacene compound according to example embodiments may have a molecular weight of about 300 to about 3,000. Within the range of the molecular weight, the heteroacene compound may be relatively easy to handle.

Examples of the heteroacene compound may be compounds represented by Chemical Formula 7-1. The compounds may be synthesized by a ring closure reaction of the intermediates represented by Chemical Formula 3-1.

[Chemical Formula 7-1]

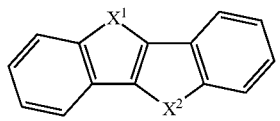
(1)

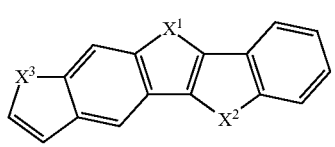
(2)

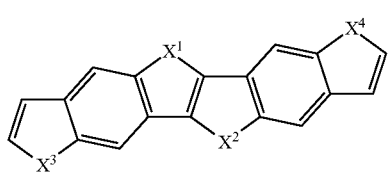
(3)

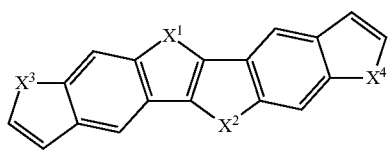
(4)

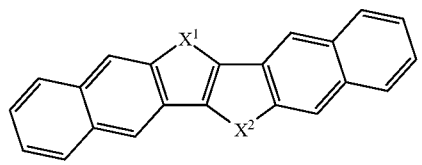
(5)

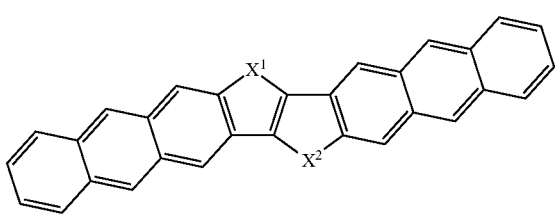
(6)

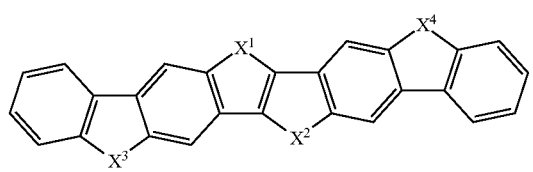
(7)

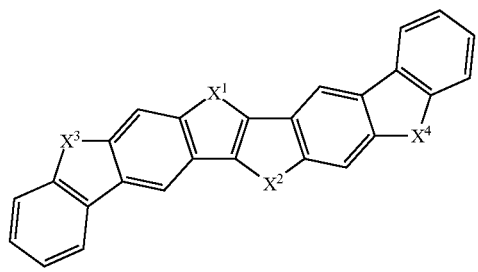
(8)

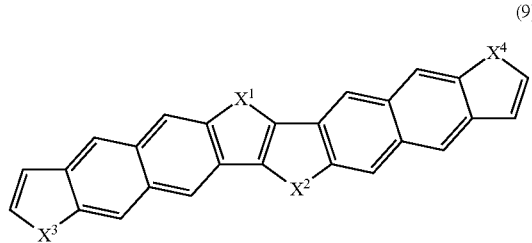
(9)

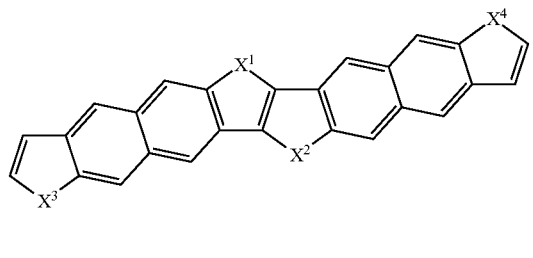
(10)

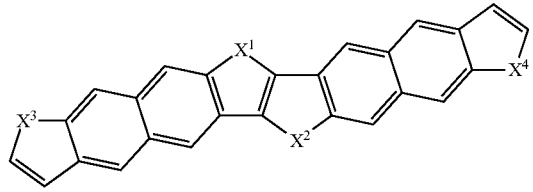
(11)

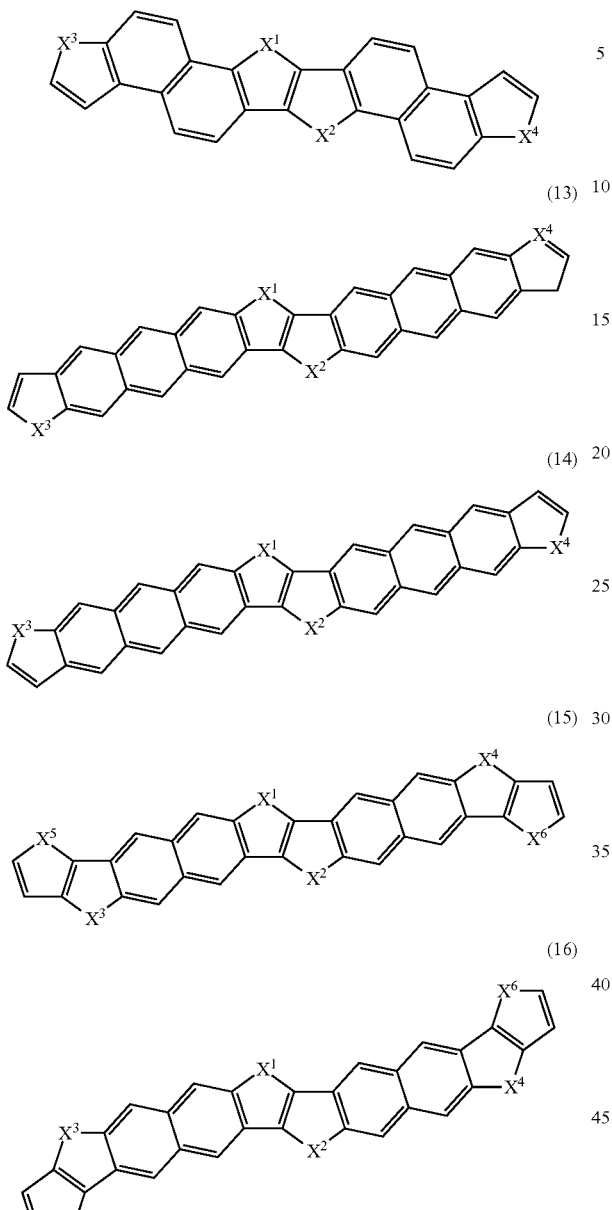

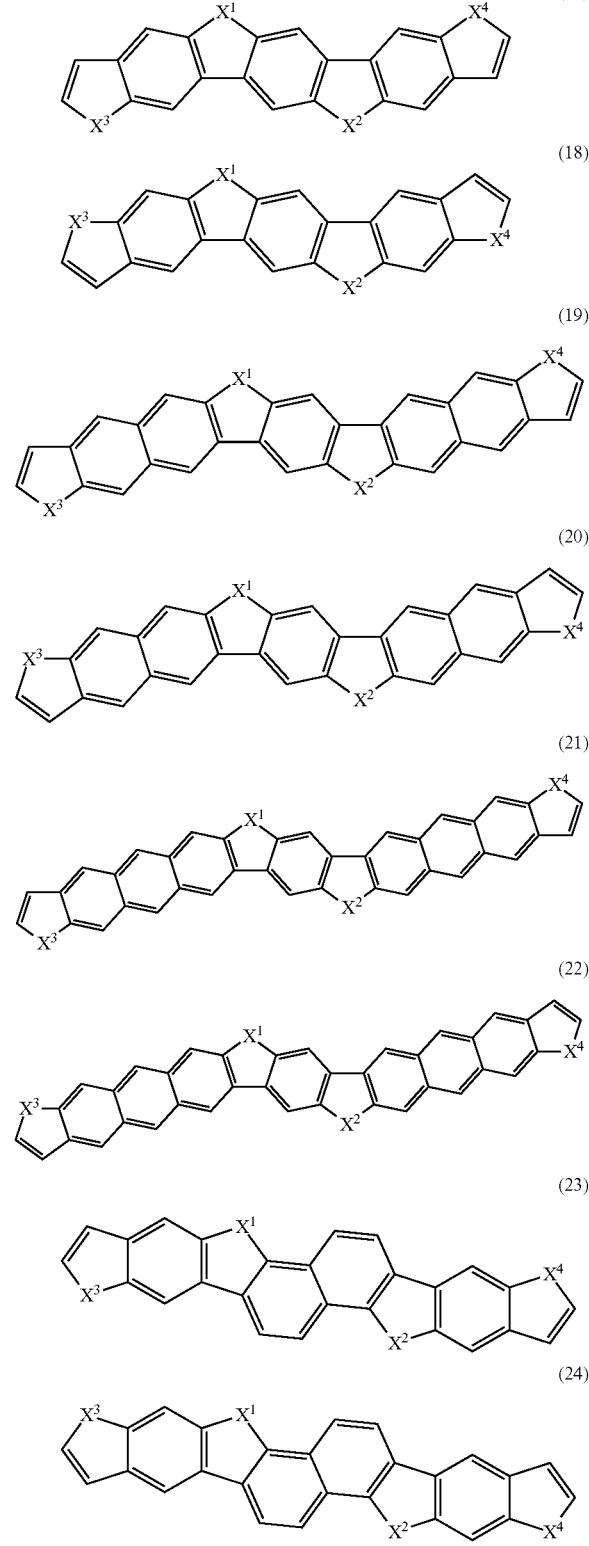

[Chemical Formula 7-2]

In Chemical Formula 7-1, each of $X^1$ and $X^2$ is independently one of O, S, Se, and Te, each of $X^3$, $X^4$, $X^5$, and $X^6$ is independently one of O, S, Se, Te, NN—$R^x$, and $C(R^y)$=$C(R^z)$, wherein each of $R^x$, $R^y$, and $R^z$ is independently one of hydrogen and a linear or branched $C_1$ to $C_{10}$ alkyl group.

In Chemical Formula 7-1, each aromatic ring may be substituted with a substituent, for example, a $C_1$ to $C_{10}$ linear or branched alkyl group.

Examples of the heteroacene compound may be compounds represented by Chemical Formula 7-2. The compounds may be synthesized by a ring closure reaction of the intermediates represented by Chemical Formula 4-1 or 4-2.

In Chemical Formula 7-2, each of $X^1$ and $X^2$ are independently one of O, S, Se, and Te, and each of $X^3$ and $X^4$ are independently one of O, S, Se, Te, NN—$R^x$, and $C(R^y)$=$C(R^z)$, wherein each of $R^x$, $R^y$, and $R^z$ are independently one of hydrogen and a linear or branched $C_1$ to $C_{10}$ alkyl group.

In Chemical Formulae 7-1 and 7-2, hydrogen of each aromatic ring may be replaced by a substituent, for example, a $C_1$ to $C_{30}$ linear or branched alkyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

Example embodiments provide an organic thin film including the heteroacene compound and an electronic device including the organic thin film.

The organic thin film according to example embodiments includes the heteroacene compound, so it may be applied to an organic semiconductor layer, or a carrier transport layer, e.g., a channel layer, for an electronic device. The electronic device including the same may have improved electrical properties, e.g., relatively high charge mobility as well as improved processability and workability.

The organic thin film may be manufactured by depositing the heteroacene compound on a substrate according to the general method, or dissolving the heteroacene compound in an organic solvent and then coating the same at room temperature according to a solution process. If required, heating treatment may be performed after the deposition or coating process to further enhance the densification and uniformity of the thin film.

Particularly, the organic solvent may include at least one kind of general organic solvent, for example, at least one kind of an aliphatic hydrocarbon solvent (e.g., hexane and/or heptane); an aromatic solvent (e.g., toluene, pyridine, quinoline, anisole, mesitylene and/or xylene); a ketone-based solvent (e.g., methyl isobutyl ketone, 1-methyl-2-pyrrolidinone, cyclohexanone and/or acetone); an ether-based solvent (e.g., tetrahydrofuran and/or isopropyl ether); an acetate-based solvent (e.g., ethyl acetate, butyl acetate and/or propylene glycol methyl ether acetate); an alcohol-based solvent (e.g., isopropyl alcohol and/or butanol); an amide-based solvent (e.g., dimethyl acetamide and/or dimethyl formamide); a silicone-based solvent; and a mixture of the solvents. The amount of the heteroacene compound dissolved in the organic solvent may be adequately selected and determined by a person of ordinary skill in the art, for example, in a range of about 0.01 wt % to about 50 wt % of the total solvent in view of solubility and coating property.

The method of providing an organic thin film may include thermal deposition, vacuum deposition, laser deposition, screen printing, printing, imprinting, spin casting, dipping, ink jetting, roll coating, flow coating, drop casting, spray coating, and/or roll printing, but is not limited thereto. The heat treatment may be performed at about 80 to about 250° C. for about 1 minute to about 2 hours, but is not limited thereto.

The thickness of the organic thin film may be adjusted according to the usage and the case considering the kinds of the used compound and solvent by a person of ordinary skill in the art, and for example, in a range of about 200 Å to about 10,000 Å.

Examples of electronic devices including the organic thin film may include a transistor, an organic light emitting diode (OLED), a photovoltaic device, a solar cell, a laser device, a memory, a sensor, etc., and the organic thin film may be applied to each device according to the general process commonly known in the art.

For example, the transistor includes: a gate electrode disposed on a substrate; a source electrode and a drain electrode facing each other and defining a channel region; an insulation layer electrically insulating the source electrode and drain electrode and the gate electrode; and an active layer including the heteroacene compound formed in the channel region.

The active layer may be obtained by depositing the heteroacene compound, or applying a composition including the heteroacene compound to a solution process, e.g., screen printing, printing, spin coating, dipping, ink jetting, etc. When the active layer is formed by the solution process, the process cost may be reduced, and a wide area device may be effectively manufactured.

Figure 2:
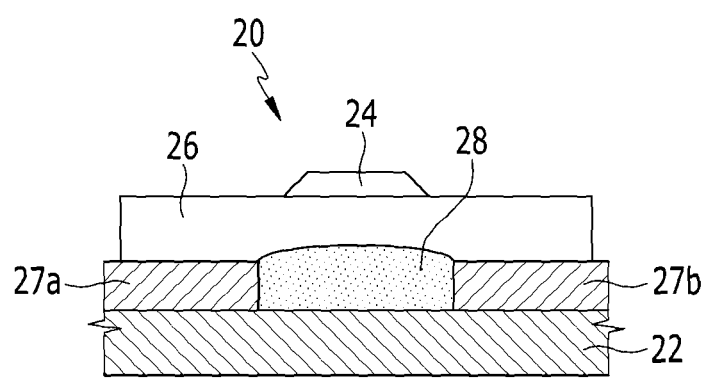
FIG. 2 is a schematic cross-sectional view showing a transistor according to example embodiments.

FIGS. 1 and 2 are schematic cross-sectional views showing a transistor according to example embodiments. The transistor according to example embodiments may be a thin film transistor. The thin film transistor may be a thin film having a thickness of several nanometers to several microns.

Referring to FIG. 1, a transistor 10 includes a substrate 12, a gate electrode 14 disposed on the substrate, and an insulation layer 16 covering the gate electrode 14. A source electrode 17a and a drain electrode 17b defining a channel region are provided on the insulation layer 16, and an active layer 18 is provided in the channel region. The active layer 18 includes the heteroacene compound.

Referring to FIG. 2, a transistor 20 includes a source electrode 27a and a drain electrode 27b defining a channel region and that are formed on a substrate 22, and an active layer 28 formed in the channel region. The active layer 28 includes the heteroacene compound. An insulation layer 26 is formed to cover the source electrode 27a, the drain electrode 27b, and the active layer 28, and a gate electrode 24 is formed thereon.

The substrates 12 and 22 may include an inorganic material, an organic material, or a composite of an inorganic material and an organic material. The organic material may include, for example, a plastic, e.g., polyethylene naphthalate (PEN), polyethylene terephthalate (PET), polycarbonate, polyvinyl alcohol, polyacrylate, polyimide, polynorbornene, and polyethersulfone (PES), and the inorganic material may include, for example, glass or metal.

In addition, the gate electrodes 14 and 24, source electrodes 17a and 27a, and drain electrodes 17b and 27b may include a generally-used metal, particularly, gold (Au), silver (Ag), aluminum (Al), nickel (Ni), or indium tin oxide (ITO), but it is not limited thereto.

The insulation layers 16 and 26 may include a generally-used insulator having a relatively high dielectric constant, particularly a ferroelectric insulator, e.g., $Ba_{0.33}Sr_{0.66}TiO_3$ (BST, barium strontium titanate), $Al_2O_3$, $Ta_2O_5$, $La_2O_5$, $Y_2O_3$, and $TiO_2$; an inorganic insulator such as $PbZr_{0.33}Ti_{0.66}O_3$ (PZT), $Bi_4Ti_3O_{12}$, $BaMgF_4$, $SrBi_2(TaNb)_2O_9$, $Ba(ZrTi)O_3$ (BZT), $BaTiO_3$, $SrTiO_3$, $SiO_2$, $SiN_x$ (x is determined depending on the valence of Si), AlON (aluminum oxynitride), etc.; or an organic insulator such as polyimide, benzocyclobutane (BCB), parylene, polyacrylate, polyvinyl alcohol, polyvinylphenol, etc., but it is not limited thereto.

Figure 3:
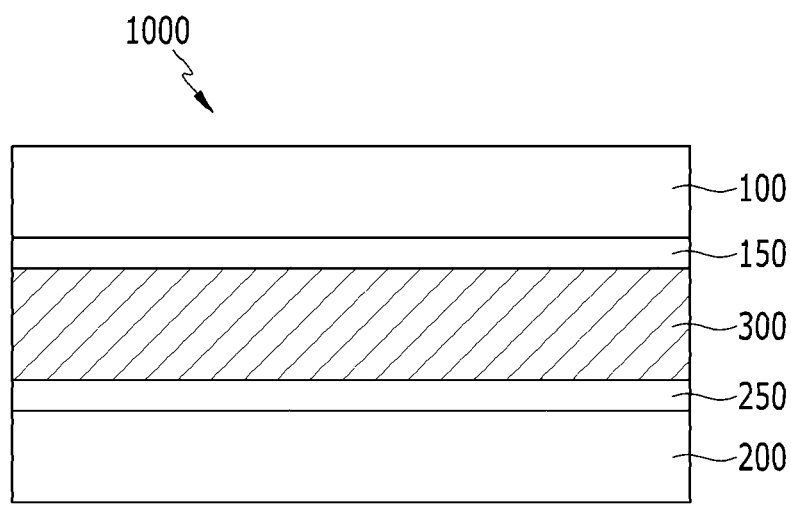
FIG. 3 is a schematic cross-sectional view showing a solar cell according to example embodiments.

FIG. 3 is a cross-sectional view showing a solar cell 1000 according to example embodiments. Referring to FIG. 3, a solar cell includes a first electrode 100 and a second electrode 200, and a photoactive layer 300 positioned between the first electrode 100 and the second electrode 200.

A substrate (not shown) may be positioned at the first electrode 100 or the second electrode 200, and may be made of a light-transmitting material. The light-transmitting material may include, for example, an inorganic material (e.g., glass), or an organic material (e.g., polycarbonate, polymethylmethacrylate, polyethylene terephthalate, polyethylene naphthalate, polyamide, polyethersulfone, or a combination thereof).

One of the first electrode 100 and the second electrode 200 is an anode and the other is a cathode. One of the first electrode 100 and second electrode 200 may be a light-transmitting electrode, and light may enter toward the light-transmitting electrode. The light-transmitting electrode may be made of, for example, a conductive oxide (e.g., indium tin oxide (ITO)), indium doped zinc oxide (IZO), tin oxide ($SnO_2$), aluminum-doped zinc oxide (AZO), and/or gallium-doped zinc oxide (GZO), or a transparent conductor of a conductive carbon composite (e.g., carbon nanotubes (CNT) or graphenes). At least one of the first electrode 100 and the second electrode 200 may be an opaque electrode, which may be made of an opaque conductor, for example, aluminum (Al), silver (Ag), gold (Au), and/or lithium (Li).

The photoactive layer 300 includes the heteroacene compound.

First and second auxiliary layers 150 and 250 may be positioned between the first electrode 100 and the photoactive layer 300 and between the second electrode 200 and the photoactive layer 300, respectively. The first and second auxiliary layers 150 and 250 may increase charge mobility between the first electrode 100 and the photoactive layer 300 and between the second electrode 200 and the photoactive layer 300. The first and second auxiliary layers 150 and 250 may be at least one selected from, for example, an electron injection layer (EIL), an electron transport layer, a hole injection layer (HIL), a hole transport layer, and a hole blocking layer, but are not limited thereto. One or both of the first and second auxiliary layers 150 and 250 may be omitted.

The photoactive layer 300 may have a tandem structure where at least two thereof are stacked.

Figure 4:
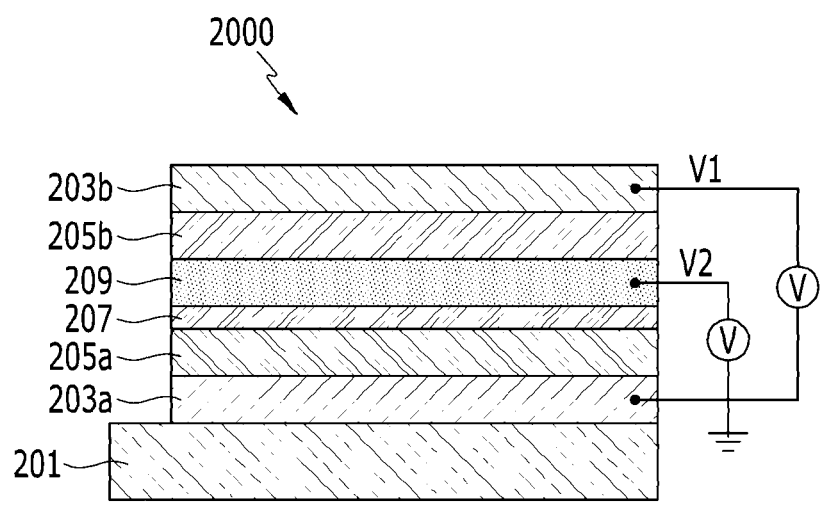
FIG. 4 is a sectional view of an organic light-emitting display apparatus according to some example embodiments.

FIG. 4 is a sectional view of an organic light-emitting display apparatus 2000 according to some example embodiments.

Referring to FIG. 4, a first electrode 203*a* and a second electrode 203*b* are positioned on a substrate 201, a first emission layer 205*a* is positioned on the first electrode 203*a*, and a second emission layer 205*b* is positioned under the second electrode 203*b*.

The substrate 201 may include a material selected from the group consisting of glass, quartz, silicon, a synthetic resin, a metal plate, and a combination thereof. The synthetic resin may include polyethylenenaphthalate (PEN), polyethyleneterephthalate (PET), polycarbonate, polyvinylalcohol, polyacrylate, polyimide, polynorbornene and/or polyethersulfone (PES), etc. The metal plate may include a stainless steel foil and/or an aluminum foil, etc.

The first electrode 203*a* may include a material having a work function of about 4.3 eV to about 5.0 eV, about 4.3 eV to about 4.7 eV, or about 4.3 eV to about 4.5 eV. According to example embodiments, the material may include aluminum (Al), copper (Cu), magnesium (Mg), molybdenum (Mo) and/or an alloy thereof, etc. In addition, these metals may be laminated to provide a first electrode. The first electrode 203*a* may have a thickness of about 20 to about 100 nm.

The second electrode 203*b* may include a material having a work function of about 2.3 eV to about 2.7 eV or about 2.5 eV to about 2.7 eV. According to example embodiments, the second electrode 203*b* may include Ba:Al. The second electrode 203*b* may have a thickness of about 20 to about 100 nm.

The first emission layer 205*a* and the second emission layer 205*b* include the heteroacene compound.

A middle electrode 209 is positioned between the first emission layer 205*a* and the second emission layer 205*b*. The middle electrode 209 may include a material having a work function of about 5.0 eV to about 5.2 eV. According to example embodiments, the material may include a conductive polymer. The conductive polymer may include polythiophene, polyaniline, polypyrrole, polyacene, polyphenylene, polyphenylenevinylene, a derivative thereof, a copolymer thereof, or a mixture thereof.

A buffer layer 207 may be positioned between the first emission layer 205*a* and the middle electrode 209, and may include a material selected from the group consisting of a metal oxide, a polyelectrolyte, and combinations thereof. The combination thereof refers to the metal oxide and polyelectrolyte being mixed or laminated to provide a multi-layer. In addition, the different kinds of metal oxide or polyelectrolyte may be laminated.

Figure 5:
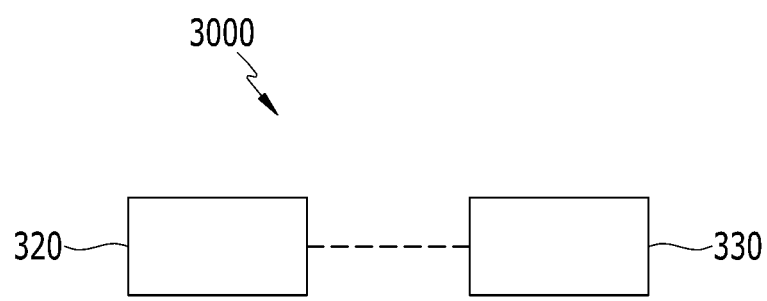
FIG. 5 is a view showing a sensor according to example embodiments.

FIG. 5 is a view showing a sensor 3000 according to example embodiments.

Referring to FIG. 5, a sensor 3000 (for example a gas sensor, light sensor, energy sensor, but example embodiments are not limited thereto) includes at least one electrode 320 configured to output a signal to a processor 330. The processor 330 may include a microprocessor, but example embodiments are not limited thereto. The electrode 320 may include the heteroacene compound.

Hereinafter, the embodiments are illustrated in more detail with reference to examples. However, these are examples, and the present disclosure is not limited thereto.

EXAMPLES

Example 1: Synthesis of Intermediate of Heteroacene Compound and Heteroacene Compound

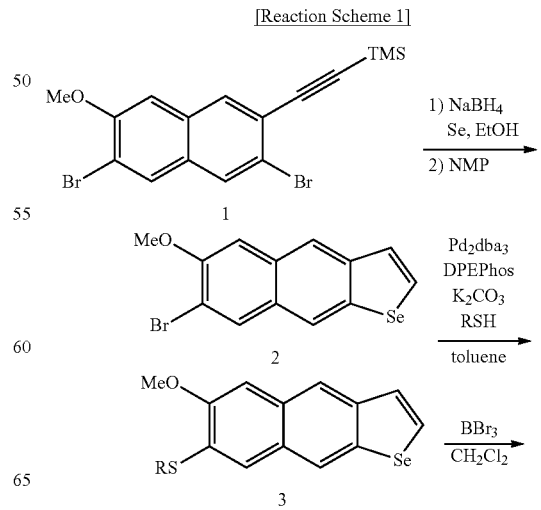

[Reaction Scheme 1]

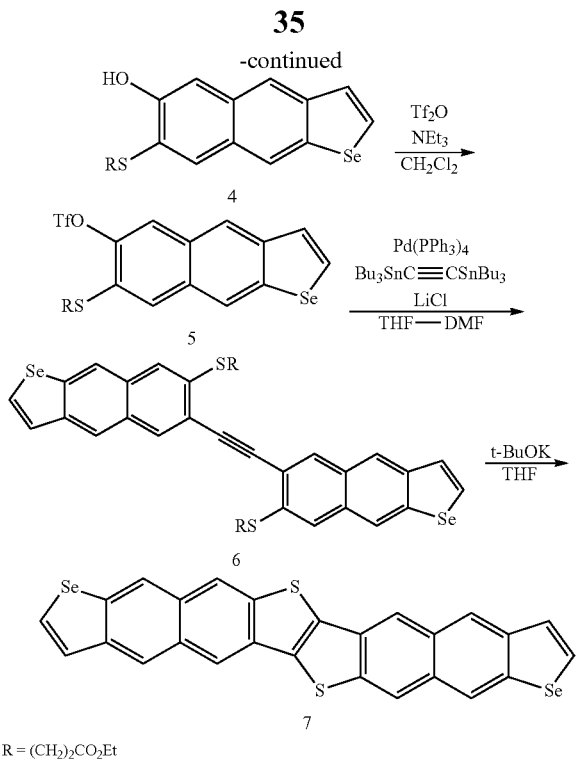

R = (CH$_2$)$_2$CO$_2$Et i) Synthesis of Compound (2)

Selenium powder (6.3 g, 80 mmol) is put in a flask and then, suspended in ethanol (300 mL). Then, sodium borohydride (3.0 g, 80 mmol) is added thereto at 0° C., and the mixture is stirred for one hour. Then, NMP (800 mL) and a compound (1) (30 g, 73 mmol) are added thereto, and the mixture is stirred at 185° C. for day and night. Then, a saturated ammonium chloride solution and water are added thereto, precipitating a solid. The solid is dissolved in chloroform, and the solution is passed through a silica pad and then, concentrated. Then, a resulting material is repre-cipitated in chloroform-methanol to obtain 18 g of a compound (2) (a yield: 70%).

$^1$H NMR (CDCl$_3$, 300 MHz) 4.03 (s, 3H), 7.24 (s, 1H), 7.61 (d, 1H, J=6.0 Hz), 8.01 (d, 1H, J=6.0 Hz), 8.10 (s, 1H), 8.20 (s, 1H), 8.23 (s, 1H).

ii) Synthesis of Compound (3)

The compound (2) (15 g, 44 mmol), potassium carbonate (15.2 g), ethyl 3-mercaptopropionate (6.7 mL, 53 mmol), tris(dibenzylideneacetone)dipalladium (0) (4 g), bis[2-(di-phenylphosphino) phenyl]ether (4.7 g), and toluene (400 mL) are put in a flask and stirred at 110° C. for day and night. Subsequently, a saturated ammonium chloride solution and water are added thereto, and a water layer is extracted with ethylacetate. Then, an organic layer obtained therefrom is cleaned with a saline solution and then, dried with anhydrous magnesium sulfate, and then the solvent is evaporated. Then, the residue is treated through column chromatography to obtain 11.5 g of a compound (3) (a yield: 68%).

$^1$H NMR (CDCl$_3$, 300 MHz) 1.26 (t, 3H, J=7.2 Hz), 2.72 (t, 2H, J=7.2 Hz), 3.29 (t, 2H, J=7.2 Hz), 4.02 (s, 3H), 4.15 (q, 2H, J=7.2 Hz), 7.19 (s, 1H), 7.60 (d, 1H, J=6.0 Hz), 7.70 (s, 1H), 7.97 (d, 1H, J=6.0 Hz), 8.18 (s, 1H), 8.25 (s, 1H).

iii) Synthesis of Compound (4)

The compound (3) (11.5 g, 29 mmol) and dichloromethane (600 mL) are put in a flask and cooled down to −78° C. Then, a 1 M boron tribromide solution (60 mL, 60 mmol) is added thereto, and then, the temperature of the obtained mixture is slowly increased. Five hours later, a saturated ammonium chloride solution and water are added thereto, and a water layer is extracted with ethyl acetate. Subsequently, an organic layer is cleaned with a saline solution, dried with anhydrous magnesium sulfate, and passed through a silica pad, and then the solvent is evaporated to obtain 9 g of a compound (3) (a yield: 82%).

$^1$H NMR (CDCl$_3$, 300 MHz) 1.26 (t, 3H, J=7.2 Hz), 2.73 (t, 2H, J=7.2 Hz), 3.30 (t, 2H, J=7.2 Hz), 4.15 (q, 2H, J=7.2 Hz), 6.35 (brs, 1H), 7.18 (s, 1H), 7.59 (d, 1H, J=6.0 Hz), 7.69 (s, 1H), 7.96 (d, 1H, J=6.0 Hz), 8.17 (s, 1H), 8.24 (s, 1H).

iv) Synthesis of Compound (5)

The compound (4) (9 g, 24 mmol) and dichloromethane (600 mL) are put in a flask and cooled down to 0° C. Subsequently, triethylamine (9 mL) and trifluoromethane-sulfonic anhydride (5.2 mL, 31 mmol) are added thereto, and the mixture is stirred at room temperature (24° C.) for day and night. Then, a saturated ammonium chloride solution and water are added thereto, and a water layer is extracted with dichloromethane. Then, an organic layer is cleaned with a saline solution and dried with anhydrous magnesium sulfate. The residue is treated through column chromatography to obtain 3.4 g of a compound (5) (a yield: 30%).

$^1$H NMR (CDCl$_3$, 300 MHz) 1.26 (t, 3H, J=7.2 Hz), 2.69 (t, 2H, J=7.5 Hz), 3.30 (t, 2H, J=7.5 Hz), 4.12 (q, 2H, J=7.2 Hz), 7.66 (d, 1H, J=6.3 Hz), 7.86 (s, 1H), 7.99 (s, 1H), 8.09 (d, 1H, J=6.3 Hz), 8.30 (s, 1H), 8.39 (s, 1H).

v) Synthesis of Intermediate of Heteroacene Compound (Compound (6))

The compound (5) (3.4 g, 6.6 mmol), lithium chloride (1.1 g), bis(tributyltin) acetylene (1.2 g, 3.3 mmol), tetrakis (triphenylphosphine) palladium (0) (0.76 g), tetrahydrofuran (100 mL), and dimethyl formamide (100 mL) are put in a flask and then, stirred for 2 days 80° C., while blocked from light. Then, ethanol and water are added thereto, precipitating a solid. The solid is dissolved in chloroform, cleaned with a saline solution, and dried with anhydrous magnesium sulfate, and then the solvent is evaporated. The residue is treated through column chromatography to obtain 1.6 g of a compound (6) (a yield: 64%).

$^1$H NMR (CDCl$_3$, 300 MHz) 1.25 (t, 3H, J=7.2 Hz), 2.73 (t, 2H, J=7.2 Hz), 3.28 (t, 2H, J=7.2 Hz), 4.18 (q, 2H, J=7.2 Hz), 7.64 (s, 1H), 7.78 (d, 1H, J=6.0 Hz), 7.88 (s, 1H), 8.00 (d, 1H, J=6.0 Hz), 8.18 (s, 1H), 8.21 (s, 1H), 8.29 (s, 1H).

vi) Synthesis of Heteroacene Compound (Compound (7))

The compound (6) (1.5 g, 2 mmol) and tetrahydrofuran (200 mL) are put in a flask, and potassium t-butoxide (0.67 g, 6 mmol) is added thereto. The mixture is stirred at 50° C. for day and night, and then ethanol is added thereto to obtain 0.81 g of a compound (7) (a yield: 74%).

MS(MALDI-TOF-MS, m/z) 547 (M$^+$)

Example 2: Synthesis of Intermediate of Heteroacene Compound and Heteroacene Compound A heteroacene compound is synthesized according to the same method as Example 1 except for using 3-mercapto-propionic acid (5.62 g, 53 mmol) instead of the ethyl 3-mercaptopropionate in the synthesis of the compound (3) of Example 1.

Example 3: Synthesis of Intermediate of Heteroacene Compound and Heteroacene Compound A heteroacene compound is synthesized according to the same method as Example 1 except for using methyl 2-mercaptoethyl ketone (5.52 g, 53 mmol) instead of the ethyl 3-mercaptopropionate in the synthesis of the compound (3) of Example 1.

Example 4: Synthesis of Intermediate of Heteroacene Compound and Heteroacene Compound A heteroacene compound is synthesized according to the same method as Example 1 except for using 3-sulfanyl propaneamide (5.6 g, 53 mmol) instead of the ethyl 3-mercaptopropionate in the synthesis of the compound (3) of Example 1.

Example 5: Synthesis of Intermediate of Heteroacene Compound and Heteroacene Compound A heteroacene compound is synthesized according to the same method as Example 1 except for using N,N-dimethyl-3-mercaptopropionamide (7.1 g, 53 mmol) instead of the ethyl 3-mercaptopropionate in the synthesis of the compound (3) of Example 1.

Example 6: Synthesis of Intermediate of Heteroacene Compound and Heteroacene Compound A heteroacene compound is synthesized according to the same method as Example 1 except for using ethyl 2-methyl-3-sulfanylpropanoate (7.9 g, 53 mmol) instead of the ethyl 3-mercaptopropionate in the synthesis of the compound (3) of Example 1.

Example 7: Synthesis of Intermediate of Heteroacene Compound and Heteroacene Compound

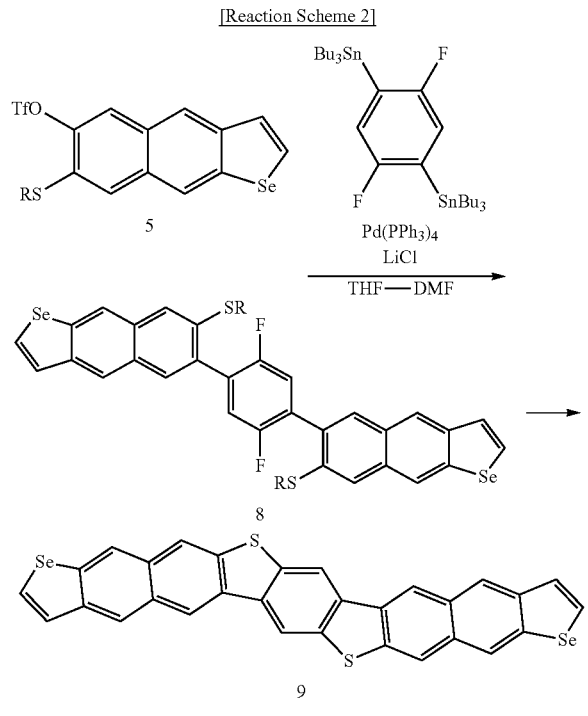

i) Synthesis of Intermediate of Heteroacene Compound (Compound (8))

The compound 5 of Example 1 (3.4 g, 6.6 mmol), lithium chloride (1.1 g), 1,4-bis(tributylstannyl)-2,5-difluorobenzene (2.3 g, 3.3 mmol), tetrakis(triphenylphosphine)palladium (0) (0.76 g), tetrahydrofuran (100 mL), and dimethyl formamide (100 mL) are put in a flask and stirred at 80° C. for 2 days while blocked from light. Then, ethanol and water are added thereto, precipitating a solid. The solid is dissolved in chloroform, cleaned with a saline solution, and dried with anhydrous magnesium sulfate, and then the solvent is evaporated. The residue is treated through column chromatography to obtain 1.6 g of a compound (8) (a yield: 64%).

ii) Synthesis of Heteroacene Compound (Compound (9))

The compound (8) (1.5 g, 2 mmol) and tetrahydrofuran (200 mL) are put in a flask, and potassium t-butoxide (0.67 g, 6 mmol) is added thereto. The mixture is stirred at 50° C. for day and night, and then ethanol is added thereto to obtain 0.81 g of a compound (9) (a yield: 74%).

Example 8: Manufacture of Organic Thin Film Transistor (OTFT)

First, chromium used as a gate electrode is deposited to be 1000 Å thick through sputtering on a cleaned glass substrate, and $SiO_2$ is deposited to form a 3000 Å-thick insulation layer thereon in a CVD method. Then, Au is deposited thereon to be 700 Å thick through sputtering, forming a source electrode and a drain electrode. The glass substrate is cleaned with isopropyl alcohol for 10 minutes and dried before coating an organic semiconductor material. In addition, the $SiO_2$ used as an insulation layer is treated with $UV/O_3$ for 30 minutes before surface modification.

Then, an OTFT device 10 having a structure shown in FIG. 1 is manufactured by dipping the substrate in n-hexane solution of octyltrichlorosilane diluted into a concentration of 10 mM for 30 minutes, washing it with hexane and alcohol, drying it, and thermally evaporating the compound (7) synthesized according to Example 1 under high vacuum ($5 \times 10^{-6}$ torr) at a speed of 0.2 Å/sec to form a 1000 Å-thick active layer 18.

While this disclosure has been described in connection with what is presently considered to be practical example embodiments, it is to be understood that the present inventive concepts are not limited to the disclosed embodiments, but, on the contrary, is intended to cover various modifications and equivalent arrangements included within the spirit and scope of the appended claims.

What is claimed is:
1. An intermediate of a heteroacene compound represented by Chemical Formula 3-1 1:

[Chemical Formula 3-1]

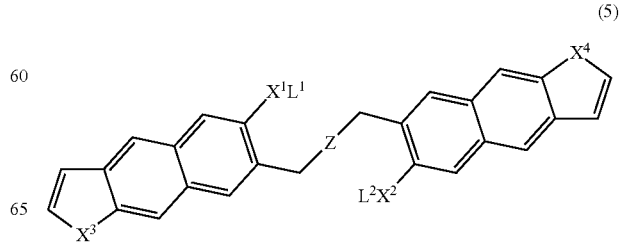

(5)

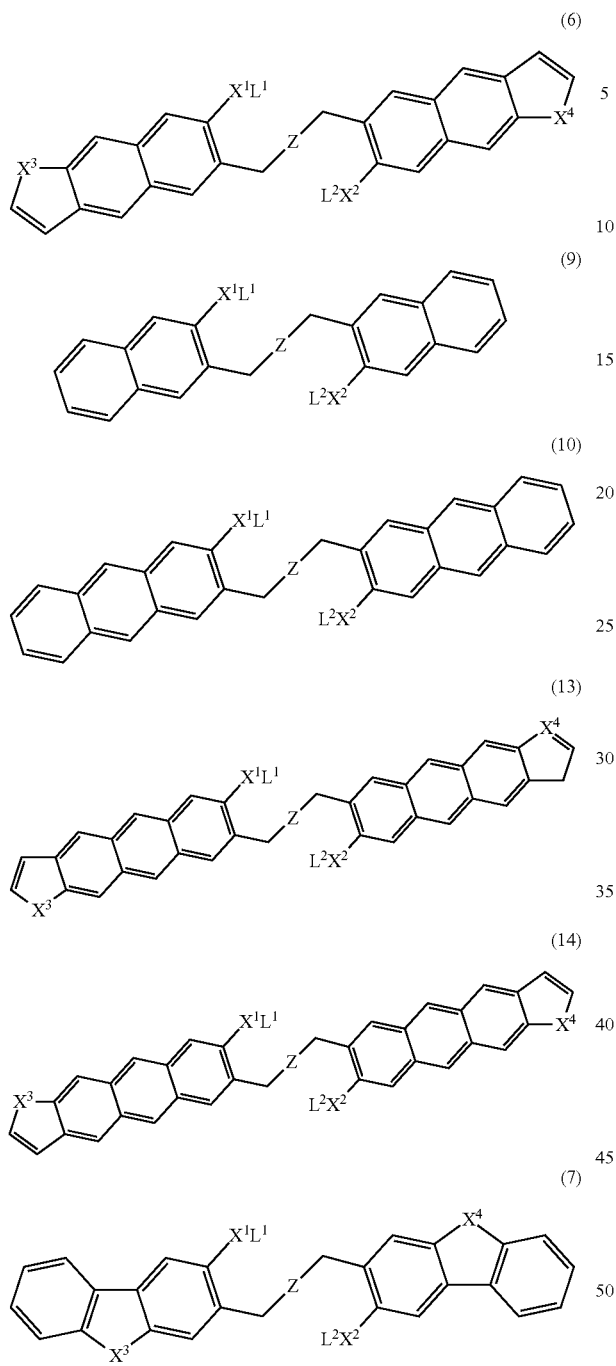

wherein, in Chemical Formula 3-1,

Z is one of an ethenylene group and an ethynylene group, each of $X^1$ and $X^2$ is independently one of O, S, Se, and Te, each $X^3$ and $X^4$ are independently one of O, S, Se, Te, N—$R^x$, and C($R^y$)=C($R^z$), wherein each of $R^x$, $R^y$ and $R^z$ is independently one of hydrogen and a linear or branched $C_1$ to $C_{10}$ alkyl group, and each of $L^1$ and $L^2$ is independently one of functional groups of Chemical Formula A and Chemical Formula B,

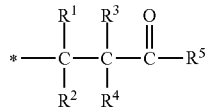

[Chemical Formula A]

wherein, in Chemical Formula A, each of $R^1$, $R^2$, and $R^3$ is independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group;

$R^4$ is one of hydrogen and a methyl group, $R^5$ is one of a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, and an amine group (NR$^x$R$^y$, wherein each of R$^x$ and R$^y$ is independently one of hydrogen, a $C_1$ to $C_{30}$ alkyl group, and a $C_6$ to $C_{30}$ aryl group), and

* indicates a linking position to $X^1$ and $X^2$,

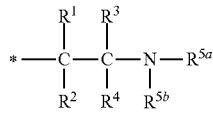

[Chemical Formula B]

wherein, in Chemical Formula B, each of $R^1$, $R^2$, and $R^3$ is independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group, $R^4$ is one of hydrogen and a methyl group, each of $R^{5a}$ and $R^{5b}$ is independently one of hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, and an amine group (NR$^x$R$^y$, wherein each of R$^x$ and R$^y$ is independently one of hydrogen, a $C_1$ to $C_{30}$ alkyl group, and a $C_6$ to $C_{30}$ aryl group), and

* indicates a linking position to $X^1$ and $X^2$.

2. The intermediate of claim 1, wherein each of the $L^1$ and $L^2$ groups is independently one of functional groups represented by Chemical Formula A-1, Chemical Formula A-2, and Chemical Formula A-3:

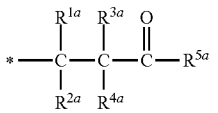

[Chemical Formula A-1]

wherein, in Chemical Formula A-1, each of $R^{1a}$, $R^{2a}$, and $R^{3a}$ is independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group, $R^{4a}$ is one of hydrogen and a methyl group, $R^{5a}$ is one of a substituted or unsubstituted $C_1$ to $C_{10}$ alkyl group and a substituted or unsubstituted $C_6$ to $C_{10}$ aryl group, and

* indicates a linking position to $X^1$ and $X^2$,

[Chemical Formula A-2]

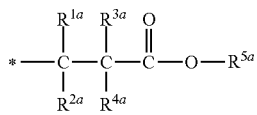

wherein, in Chemical Formula A-2, each of $R^{1a}$, $R^{2a}$, and $R^{3a}$ is independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group, and a $C_3$ to $C_{10}$ heteroaryl group, $R^{4a}$ is one of hydrogen and a methyl group, $R^{5a}$ is one of a substituted or unsubstituted $C_1$ to $C_{10}$ alkyl group and a substituted or unsubstituted $C_6$ to $C_{10}$ aryl group, and

* indicates a linking position to $X^1$ and $X^2$, and

[Chemical Formula A-3]

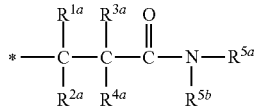

wherein, in Chemical Formula A-3, each of $R^{1a}$, $R^{2a}$, and $R^{3a}$ is independently one of hydrogen, a $C_1$ to $C_6$ alkyl group, a $C_3$ to $C_{10}$ cycloalkyl group, a $C_3$ to $C_{10}$ heterocycloalkyl group, a $C_6$ to $C_{10}$ aryl group and a $C_3$ to $C_{10}$ heteroaryl group, $R^{4a}$ is one of hydrogen and a methyl group, each of $R^{5a}$ and $R^{5b}$ is independently one of a substituted or unsubstituted $C_1$ to $C_{10}$ alkyl group and a substituted or unsubstituted $C_6$ to $C_{10}$ aryl group, and

* indicates a linking position to $X^1$ and $X^2$.

3. The intermediate of claim 1, wherein in the Chemical Formula 3-1, a hydrogen of each aromatic ring is replaced by a substituent selected from a $C_1$ to $C_{30}$ linear or branched alkyl group, a substituted or unsubstituted $C_6$ to $C_{30}$ aryl group, a substituted or unsubstituted $C_2$ to $C_{30}$ heteroacyl group, a substituted or unsubstituted C7 to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted C5 to $C_{30}$ cycloalkyl group and a substituted or unsubstituted $C_2$ to $C_{30}$ heterocycloalkyl group.

4. A synthetic method of a heteroacene compound comprising:

forming a chalcogenophene ring by reacting an intermediate of a heteroacene compound represented by Chemical Formula 3-1 with a base material:

[Chemical Formula 3-1]

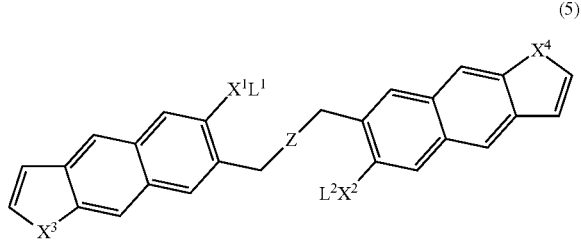

(5)

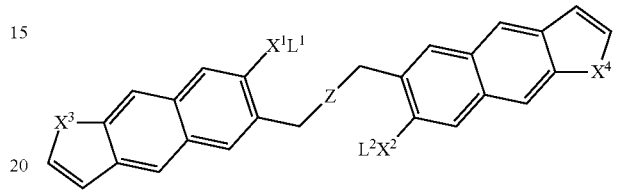

(6)

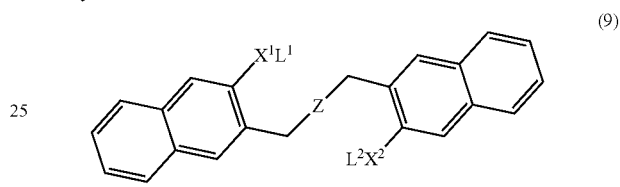

(9)

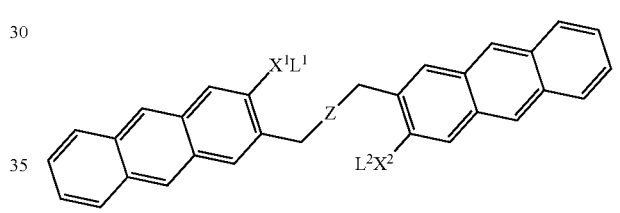

(10)

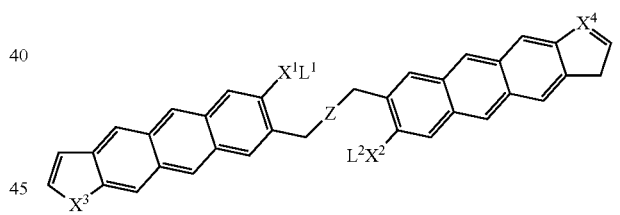

(13)

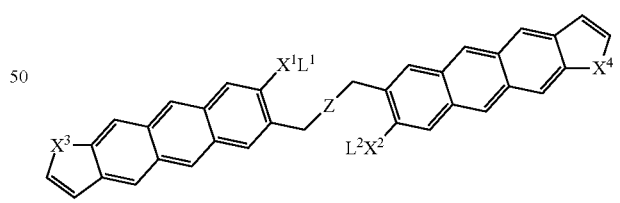

(14)

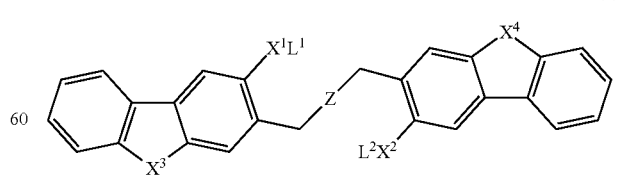

(7)

wherein, in Chemical Formula 3-1,

Z is one of an ethenylene group and an ethynylene group, each of $X^1$ and $X^2$ is independently one of O, S, Se, and Te, each of $X^3$, and $X^4$ are independently one of O, S, Se, Te, N—$R^x$, and $C(R^y)$—$C(R^z)$, wherein each of $R^x$, $R^y$ and $R^z$ is independently one of hydrogen and a linear or branched $C_1$ to $C_{10}$ alkyl group, and each of $L^1$ and $L^2$ is independently one of functional groups of Chemical Formula A and Chemical Formula B,

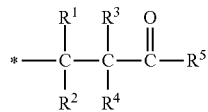

[Chemical Formula A]

wherein, in Chemical Formula A, each of $R^1$, $R^2$, and $R^3$ is independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group, $R^4$ is one of hydrogen and a methyl group, $R^5$ is a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, and an amine group ($NR^xR^y$, wherein each of $R^x$ and $R^y$ is independently one of hydrogen, a $C_1$ to $C_{30}$ alkyl group, and a $C_6$ to $C_{30}$ aryl group), and

* indicates a linking position to $X^1$ and $X^2$,

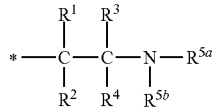

[Chemical Formula B]

wherein, in Chemical Formula B, each of $R^1$, $R^2$, and $R^3$ is independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_3$ to $C_{30}$ heterocycloalkyl group, a substituted or unsubstituted $C_6$ to $C_{30}$ aryl group, and a substituted or unsubstituted $C_3$ to $C_{30}$ heteroaryl group, $R^4$ is one of hydrogen and a methyl group, each of $R^{5a}$ and $R^{5b}$ is independently one of hydrogen, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, and an amine group ($NR^xR^y$, wherein each of $R^x$ and $R^y$ is independently one of hydrogen, a $C_1$ to $C_{30}$ alkyl group, and a $C_6$ to $C_{30}$ aryl group), and

* indicates a linking position to $X^1$ and $X^2$.

5. The method of claim 4, wherein the base material is one of metal alkoxide, metal amine, phosphine compound, and a combination thereof.

6. An electronic device comprising a heteroacene compound synthesized by the method of claim 4.